(12) United States Patent
Higginbottom et al.

(10) Patent No.: US 7,807,685 B2
(45) Date of Patent: Oct. 5, 2010

(54) THERAPEUTIC COMPOUNDS

(75) Inventors: Michael Higginbottom, Highfields Caldecote (GB); Edward D. Savory, Great Cambourne (GB); Giles A. Brown, Cambridge (GB); Viet-Anh A. Horgan, Ely (GB); Emma J. Chapman, Cambridge (GB)

(73) Assignee: CBT Development Limited, London (GB)

( * ) Notice: Subject to any disclaimer, the term of this patent is extended or adjusted under 35 U.S.C. 154(b) by 0 days.

(21) Appl. No.: 11/823,377

(22) Filed: Jun. 26, 2007

(65) Prior Publication Data

US 2008/0076776 A1 Mar. 27, 2008

Related U.S. Application Data

(60) Provisional application No. 60/837,146, filed on Aug. 11, 2006.

(30) Foreign Application Priority Data

Jun. 27, 2006 (SE) .................................... 0601398

(51) Int. Cl.
*A61K 31/52* (2006.01)
*C07D 473/00* (2006.01)

(52) U.S. Cl. .................................. 514/263.23; 544/277

(58) Field of Classification Search ............ 514/263.23; 544/277
See application file for complete search history.

(56) References Cited

U.S. PATENT DOCUMENTS 5,877,180 A    3/1999    Linden et al.

FOREIGN PATENT DOCUMENTS

| EP | 0 601 322 A | 6/1994 |
|---|---|---|
| GB | 2 396 108 A | 6/2004 |
| WO | WO-2004052377 A1 | 6/2004 |
| WO | WO-2004078183 A1 | 9/2004 |
| WO | WO-2004078184 A1 | 9/2004 |
| WO | WO-2004079329 A2 | 9/2004 |
| WO | WO-2005084653 A2 | 9/2005 |

OTHER PUBLICATIONS

Miyai et al., "Synthesis and Anti-Deoxyribonucleic Acid Virus Activity of Certain 9-beta-Arabinofuranosyl-2-substitued Adenine Derivatives", J. of Med. Chem., vol. 17, 1974 242-244.

Keeling, Suzanne E. et al., "The Discovery and Synthesis of Highly Potent, A2a Receptor Agonists," Bioorganic & Medicinal Chemistry Letters, 2000, vol. 10, pp. 403-406.

Doytchinova, I. et al., "Adenosine A2A Receptor agonists: CoMFA-based selection of the most predictive conformation," SAR and QSAR in Environmental Research, 2002, vol. 13, No. 2, pp. 227-235.

Zhan-Guo Gao et al., "2-Substituted adenosone derivatives: affinity and efficacy at four subtypes of human adenosine recptors," Biochem. Pharamacology, vol. 68, 2004, 1985-1993.

Rieger et al., "Design, Synthesis, and Evaluation of Novel $A_{2A}$ Adenosine Receptor Agonists," J.Med.Chem.,vol. 44, 2001, 531-539.

*Primary Examiner*—Kamal A Saeed
*Assistant Examiner*—Samantha L Shterengarts
(74) *Attorney, Agent, or Firm*—Edwards Angell Palmer & Dodge LLP; Jeffrey Hsi; Weiying Yang

(57) ABSTRACT

Compounds of formula (I) below are disclosed. Their use as medicaments is described, in particular for the treatment of pain or inflammation:

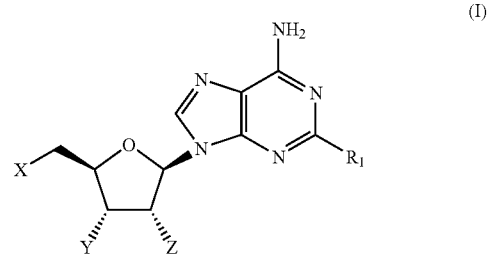

(I)

wherein:

when $X=Y=Z=OH$, $R_1$ is $OCH_2CF_2CF_3$, phenoxy (substituted with 3-(4-trifluoromethylphenyl), 3,4-dichloro, (3-trifluoromethyl,4-fluoro), (3-trifluoromethyl,4-chloro), (3-chloro, 4-cyano), or 3,5-bis(trifluoromethyl)), 1-piperazinyl(4-(3,4-dichlorophenyl)), phenyl (substituted with 3,4-dichloro, 3,5-difluoro, 3,5-bis(trifluoromethyl) or 3,4,5-trifluoro) or 2-benzofuranyl; or when $X=Y=OH$ and $Z=OMe$, $R_1$ is $OCH_3$, $OCH_2CHF_2$, $OCH_2$cyclopentyl, O-(2,5-difluorophenyl) or (S)-sec-butylamino; or when $X=H$ and $Y=Z=OH$, $R_1$ is n-hexylamino or cyclopentylamino; or when (IV) $X=Z=OH$ and $Y=H$, $R_1$ is cyclopentylamino;

or a pharmaceutically acceptable salt thereof.

5 Claims, No Drawings

THERAPEUTIC COMPOUNDS

CROSS-REFERENCE TO RELATED APPLICATIONS

This application claims benefit of Swedish application No. 0601398-1 filed Jun. 27, 2006 and U.S. application 60/837,146 filed Aug. 11, 2006, the entire contents of each is herein incorporated by reference.

TECHNICAL FIELD

This invention relates to compounds that are adenosine receptor agonists, and to their use as medicaments, in particular as analgesic or anti-inflammatory compounds, and to methods of preventing, treating, or ameliorating pain or inflammation using these compounds.

BACKGROUND ART

Adenosine is a ubiquitous local hormone/neurotransmitter that acts on four known receptors, the adenosine A1, A2A, A2B and A3 receptors. Adenosine generally serves to balance the supply and demand of energy in tissues. For example, in the heart released adenosine slows the heart by an A1 receptor mediated action in the nodes and atria, while simultaneously dilating the coronary artery to increase energy supply. Similarly, during inflammation adenosine serves to inhibit inflammatory activity, while in conditions of excessive nerve activity (such as epilepsy) adenosine inhibits nerve firing. This system, or a variant on it, is present in all tissues.

Adenosine itself can be used to diagnose and treat supraventricular tachycardia. Adenosine A1 receptor agonists are known to act as powerful analgesics (Sawynok, J. Eur J. Pharmacol. (1998) 347, 1-11; Giffin et al, (2003) 23, 4, 287-292). A2a agonists have recently been shown to give significant pain relief in conditions of increased pain sensitivity (such as neuropathic and inflammatory hyperalgesia) (WO 2004/052377; WO 2004/078183; WO 2004/078184; WO 2005/084653) and are known to have anti-inflammatory activity (see, for example U.S. Pat. No. 5,877,180; WO 99/34804; Linden et al, Expert Opin. Investig. Drugs (2005) 14, 7, 797-806; Sitkovsky et al, TRENDS in Immunology (2005) 26, 6, 299-304; Linden et al, Journal of Immunology (2006) 117, 2765-2769; Cronstein et al (2004) 25, 1, 33-39). In experimental animals, A2A receptor agonists have been shown to be effective against a wide variety of conditions including sepsis (Linden et al, The Journal of Infectious Diseases (2004) 189, 1897-1904), arthritis (Cohen et al, J. Orthop. Res. (2005) 23, 5, 1172-1178; Cohen et al, J. Orthop. Res. (2004) 22, 2, 427-435), and ischaemia/reperfusion injury arising from renal, coronary or cerebral artery occlusion (see, for example Day et al, J. Clin. Invest, (2003) 112, 883-891; Linden et al, Am. J. Physiol. Gastrointest. Liver Physiol. (2004) 286, G285-G293; Linden et al, Am J. Physiol. (1999) 277, F404-F412; Schlack et al, J. Cardiovasc. Pharmacol. (1993) 22, 89-96; Zu et al, J. Cardiovasc. Pharmacol. (2005) 46, 6, 794-802; Linden et al, Am J. Physiol. Heart Circ. Physiol. (2005) 288, 1851-1858; Kennedy et al, Current Opinion in Investigational Drugs (2006) 7, 3, 229-242). The common factor in these conditions is a reduction in the inflammatory response caused by the inhibitory effect of this receptor on most, if not all, inflammatory cells. A2a agonists are also known to promote wound healing (Montesinos, Am. J. Pathol. (2002) 160, 2009-2018).

However, the ubiquitous distribution of adenosine receptors means that administration of adenosine receptor agonists causes adverse side effects. This has generally precluded the development of adenosine-based therapies. Selective A1 receptor agonists cause bradycardia. A2A receptor agonists cause widespread vasodilation with consequent hypotension and tachycardia. The first selective A2A receptor agonist (2-[4-(2-carboxyethyl)phenylethylamino]-5'-N-ethylcarboxamidoadenosine, or CGS21680), was tested in a Phase 2A clinical trial as a potential anti-hypertensive. However, administration of this compound caused a large fall in blood pressure and consequent increase in cardiac output. This has prevented use of CGS21680 as a medicament. Webb et al. (J. Pharmacol Exp Ther (1991) 259, 1203-1212), Casati et al. (J Pharmacol Exp Ther (1995) 275(2):914-919), and Bonnizone et al. (Hypertension. (1995) 25, 564-9) show that selective A2A adenosine receptor agonists cause hypotension and tachycardia. The degree of tachycardia induced is sufficient to preclude their use as medicaments. Alberti et al. (J Cardiovasc Pharmacol. 1997 Sep.; 30(3):320-4) discloses that selective A2A adenosine receptor agonists are potent vasodilators that reduce blood pressure and induce marked increments in heart rate and plasma renin activity. These side effects preclude their use as medicaments.

U.S. Pat. No. 5,877,180 relates to agonists of A2A adenosine receptors which are stated to be effective for the treatment of inflammatory diseases. The preferred agonists, WRC0090 and SHA 211 (WRC0474), are disclosed to be more potent and selective than previously reported adenosine analogs such as CGS21680 and CV1808. Administration of SHA 211 or WRC0090 is considered to reduce the possibility of side effects mediated by the binding of the analogs to other adenosine receptors. However, only in vitro data relating to the activity of SHA 211 is included. There is no demonstration that any of the compounds described could be therapeutically effective in vivo without causing serious side effects. Although side effects mediated by the binding of potent and selective adenosine A2A receptor agonists to other adenosine receptors is expected to be reduced by use of such agonists, the ubiquitous distribution of adenosine receptors means that these compounds would still be expected to activate adenosine A2A receptors in normal tissue and, therefore, cause serious side effects (such as hypotension and reflex tachycardia).

Ribeiro et al. (Progress in Neurobiology 68 (2003) 377-392) is a review of adenosine receptors in the nervous system. It is stated in the concluding remarks of this article (on page 387, right column, lines 4-10 of section 8) that "as noted a long time ago, activation of adenosine receptors at the periphery is associated with hypotension, bradycardia and hypothermia . . . . These side effects have so far significantly limited the clinical usefulness of adenosine receptor agonists".

There is, therefore, a need to provide adenosine receptor agonists that can be administered with minimal side effects.

There is also a need to provide analgesics for the treatment of pain. Pain has two components, each involving activation of sensory neurons. The first component is the early or immediate phase when a sensory neuron is stimulated, for instance as the result of heat or pressure on the skin. The second component is the consequence of an increased sensitivity of the sensory mechanisms innervating tissue which has been previously damaged. This second component is referred to as hyperalgesia, and is involved in all forms of chronic pain arising from tissue damage, but not in the early or immediate phase of pain perception.

Thus, hyperalgesia is a condition of heightened pain perception caused by tissue damage. This condition is a natural response of the nervous system apparently designed to encourage protection of the damaged tissue by an injured individual, to give time for tissue repair to occur. There are two known underlying causes of this condition, an increase in sensory neuron activity, and a change in neuronal processing of nociceptive information which occurs in the spinal cord. Hyperalgesia can be debilitating in conditions of chronic inflammation (e.g. rheumatoid arthritis), and when sensory nerve damage has occurred (i.e. neuropathic pain).

Two major classes of analgesics are known: (i) non steroidal anti-inflammatory drugs (NSAIDs) and the related COX-2 inhibitors; and (ii) opiates based on morphine. Analgesics of both classes are effective in controlling normal, immediate or nociceptive pain. However, they are less effective against some types of hyperalgesic pain, such as neuropathic pain. Many medical practitioners are reluctant to prescribe opiates at the high doses required to affect neuropathic pain because of the side effects caused by administration of these compounds (such as restlessness, nausea, and vomiting), and the possibility that patients may become addicted to them. NSAIDs are much less potent than opiates, so even higher doses of these compounds are required. However, this is undesirable because these compounds cause irritation of the gastro-intestinal tract.

There is, therefore, a need to provide analgesics, particularly anti-hyperalgesics, that are sufficiently potent to control pain perception in neuropathic and other hyperalgesic syndromes, and which do not have serious side effects or cause patients to become addicted to them.

Spongosine (also known as 2-methoxyadenosine) is known to be a weak, non-selective adonosine receptor agonist (Ueeda et al J Med Chem (1991) 34, 1334-1339). This compound caused 25% inhibition of carageenan-induced inflammation in rats at 20 mg/kg po. However, reductions in mean blood pressure (41%), and in heart rate (25%) were also observed after administration of this compound at this dose (Bartlett et al. (J. Med. Chem. (1981) 24, 947-954)).

The applicant has previously found that spongosine surprisingly is an effective analgesic at doses as much as one hundred times lower than would be expected to be required to have an analgesic effect based on the known affinity of this compound for adenosine receptors. At these doses, spongosine does not cause the significant side effects associated with higher doses of this compound, or other adenosine receptor agonists. Thus, the therapeutic effects of spongosine can be separated from its side effects. The activity of spongosine as an analgesic is the subject of International patent application no. PCT/GB03/05379, and the activity of compounds related to spongosine as analgesics is the subject of International patent application no. PCT/GB04/00935. Use of spongosine and related compounds to treat inflammation and other disorders is the subject of International patent application no. PCT/GB04/000952.

The Applicant has found that spongosine, and the related compounds described in PCT/GB04/00935 and PCT/GB04/000952, have increased affinity for adenosine receptors at pH below pH 7.4. It is believed that this property explains the surprising activity of these compounds at low doses.

The Applicant has found, however, that for some substituted adenosines which have increased affinity for adenosine receptors at pH below pH 7.4, closely related compounds do not retain this desired activity. This has made it extremely difficult to identify additional substituted adenosines that may be used as medicaments without causing serious side effects, since it has not been possible to predict which particular substituted adenosines will have increased affinity for adenosine receptors at reduced pH. By way of illustration of this unpredictability, the Table below gives the Ki (nM) values at rat adenosine A2a receptors at pH 5.5 and 7.4 for compounds of a 2-aminoalkyl adenosine series and a 5'-amido adenosine series (these values were calculated using similar binding experiments to those described in relation to Example 1 below):

| Structure | (Ki) nM (pH 5.5) | (Ki) nM (pH 7.4) |
|---|---|---|
| 2-Aminoalkyl adenosines | | |
| $NHCH_3$ | 24 | 1356 |
| $NHCH_2CH_3$ | 130 | 1200 |
| $NHCH_2CH_2CH_3$ | 1900 | 1900 |
| $NHCH_2CH_2CH_2CH_3$ | 47 | 17 |
| $NHCH_2CH_2CH_2CH_2CH_2CH_3$ | 0.7 | 290 |
| 5'-Amido adenosines | | |
| $CONH_2$ | 9.4 | 270 |
| $CONHCH_3$ | 11 | 55 |
| $CONHCH_2CH_3$ | 5.1 | 5.1 |
| CONHcyclopropyl | 4.3 | 4.3 |
| $CONHCH(CH_3)_2$ | 4.6 | 1900 |
| $CONHCH_2CH_2CH_3$ | 35 | 35 |
| $CONHCH_2CH_2CH_2CH_3$ | 24 | 21 |

Only certain compounds in each series in the above table have increased affinity for adenosine receptors at reduced pH. In the 2-aminoalkyl series, as the alkyl chain length is increased to 3 or 4 carbons, the desired activity is lost, but recovered when the chain length is increased to 6 carbons. In the 5'-amido series, as the alkyl chain length is increased to 2 or more carbons, the desired activity is lost, with the unpredictable exception of the NHisopropyl amide which is more than 400 fold more active at pH 5.5 compared to pH 7.4.

In spite of the difficulty in identifying additional substituted adenosines with increased affinity for adenosine receptors at reduced pH from the many millions of possible compounds, the Applicant has now identified certain other compounds that also have increased affinity for adenosine receptors at reduced pH. It is thought that these compounds can be used as medicaments without causing serious side effects.

DISCLOSURE OF THE INVENTION

According to the invention there are provided adenosine receptor agonists of the following formula:

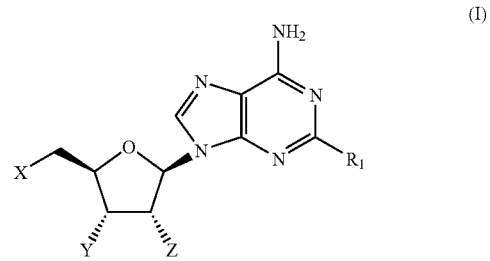

(I)

wherein:

when X=Y=Z=OH, $R_1$ is $OCH_2CF_2CF_3$, phenoxy (substituted with 3-(4-trifluoromethylphenyl), 3,4-dichloro, (3-trifluoromethyl,4-fluoro), (3-trifluoromethyl,4-chloro), (3-chloro, 4-cyano), or 3,5-bis(trifluoromethyl)), 1-piperazinyl(4-(3,4-dichlorophenyl)), phenyl (substituted with 3,4-dichloro, 3,5-difluoro, 3,5-bis(trifluoromethyl) or 3,4,5-trifluoro) or 2-benzofuranyl; or when X=Y=OH and Z=OMe, $R_1$ is $OCH_3$, $OCH_2CHF_2$, $OCH_2$cyclopentyl, O-(2,5-difluorophenyl) or (S)-sec-butylamino; or when X=H and Y=Z=OH, $R_1$ is n-hexylamino or cyclopentylamino; or when X=Z=OH and Y=H, $R_1$ is cyclopentylamino.

or a pharmaceutically acceptable salt thereof.

For the avoidance of doubt, reference to compounds of formula (I) below includes pharmaceutically acceptable salts of the compounds of formula (I).

Other aspects are compounds of the formulae herein wherein X, Y, and Z are OH; and wherein at least one of X, Y and Z is not OH.

Compounds of the invention are all believed to have increased affinity for adenosine receptors at pH below pH 7.4. In normal mammalian tissues extracellular pH is tightly regulated between pH 7.35 and 7.45. Some tissues experience lower pH values, particularly the lumen of the stomach (pH between 2 and 3) and the surfaces of some epithelia (for example, the lung surface pH is approximately 6.8). In pathological tissues, for example during inflammation, ischaemia and other types of damage, a reduction in pH occurs.

Because of the increased affinity of compounds of the invention for adenosine receptors at reduced pH, it is thought that the actions of these compounds can be targeted to regions of low pH, such as pathological tissues. Consequently, the doses of these compounds that are required to give therapeutic effects are much lower than would be expected based on their affinity for adenosine receptors at normal extracellular physiological pH. Since only low doses of the compounds are required, the serious side effects associated with administration of adenosine receptor agonists are avoided or minimised. This has the surprising consequence (contrary to the teaching in the art, for example in U.S. Pat. No. 5,877,180) that some adenosine receptor agonists that are low affinity and/or non-selective agonists at physiological pH (such as spongosine) can be therapeutically effective without causing serious side effects.

It is believed that compounds of formula (I) can be administered at doses well below those expected to be required based on their affinity for adenosine receptors at pH 7.4, and cause therapeutic effects at these doses without causing serious side effects.

Thus, according to the invention there is provided a compound of the invention for use as a medicament.

Any pathological condition that can be prevented or improved by agonism of adenosine A2A receptors can be prevented, treated, or ameliorated by a compound of formula (I).

According to the invention there is provided use of a compound of formula (I) in the manufacture of a medicament for the prevention, treatment, or amelioration of a pathological condition that can be improved or prevented by agonism of adenosine A2A receptors.

There is also provided according to the invention a method of prevention, treatment, or amelioration of a pathological condition that can be improved or prevented by agonism of adenosine A2A receptors, which comprises administering a compound of formula (I) to a subject in need of such prevention, treatment, or amelioration.

A person of ordinary skill in the art can readily test whether or not a pathological condition that is prevented, treated, or ameliorated by a compound of formula (I) is acting via adenosine A2A receptors. For example, this may be done by comparing the effect of the compound in an animal model of the pathological condition in the presence and absence of a selective antagonist of an adenosine A2A receptor. If the effect of the compound in the presence of the antagonist is reduced or absent compared with the effect of the compound in the absence of the antagonist, it is concluded that the compound is exerting its effect via an adenosine A2A receptor. Antagonists of adenosine A2A receptors are known to those of ordinary skill in the art (see for example Ongini et al., Farmaco. 2001 January-February; 56(1-2):87-90).

Alternatively, an adenosine A2A receptor knockout mouse may be used (Ohta A and Sitkovsky M, Nature 2001; 414: 916-20). For example, the effect of the compound on a mouse that has symptoms of the pathological condition is compared with its effect on an adenosine A2A knockout mouse that has corresponding symptoms. If the compound is only effective in the mouse that has adenosine A2A receptors it is concluded that the compound is exerting its effect via adenosine A2A receptors.

It is believed that compounds of formula (I) have analgesic and/or anti-inflammatory activity and can be administered with reduced probability and severity of side effects compared to other adenosine receptor agonists.

According to the invention there is provided use of a compound of formula (I) in the manufacture of a medicament for the prevention, treatment, or amelioration of pain, particularly hyperalgesia. There is also provided according to the invention a method of preventing, treating, or ameliorating pain (particularly hyperalgesia) which comprises administering a compound of formula (I) to a subject in need of such prevention, treatment, or amelioration.

Methods delineated herein include those wherein the subject is identified as in need of a particular stated treatment. Identifying a subject in need of such treatment can be in the judgment of a subject or a health care professional and can be subjective (e.g. opinion) or objective (e.g. measurable by a test or diagnostic method).

Compounds of formula (I) are believed to be effective in inhibiting pain perception in mammals suffering from pain, in particular neuropathic or inflammatory pain, even when administered at doses expected to give plasma concentrations well below those known to activate adenosine receptors. Therefore, it is believed that compounds of formula (I) can treat pain (particularly neuropathic and inflammatory pain) without causing the significant side effects associated with administration of other adenosine receptor agonists.

As mentioned above hyperalgesia is a consequence in most instances of tissue damage, either damage directly to a sensory nerve, or damage of the tissue innervated by a given sensory nerve. Consequently, there are many conditions in which pain perception includes a component of hyperalgesia.

According to the invention there is provided use of a compound of formula (I) as an analgesic (particularly an anti-hyperalgesic) for the prevention, treatment, or amelioration of pain (particularly hyperalgesia) caused as a result of neuropathy, including Diabetic Neuropathy, Polyneuropathy, Cancer Pain, Fibromyalgia, Myofascial Pain Syndrome, Osteoarthritis, Pancreatic Pain, Pelvic/Perineal pain, Post Herpetic Neuralgia, Rheumatoid Arthritis, Sciatica/Lumbar Radiculopathy, Spinal Stenosis, Temporo-mandibular Joint Disorder, HIV pain, Trigeminal Neuralgia, Chronic Neuropathic Pain, Lower Back Pain, Failed Back Surgery pain, back pain, post-operative pain, post physical trauma pain (including gunshot, road traffic accident, burns), Cardiac pain, Chest pain, Pelvic pain/PID, Joint pain (tendonitis, bursitis, acute arthritis), Neck Pain, Bowel Pain, Phantom Limb Pain, Obstetric Pain (labour/C-Section), Renal Colic, Acute Herpes Zoster Pain, Acute Pancreatitis Breakthrough Pain (Cancer), Dysmenorhoea/Endometriosis; or in any of the above pathological conditions where bacterial or viral infection is a cause or exacerbates the condition.

According to the invention there is also provided use of a compound of formula (I) as an analgesic (particularly and anti-hyperalgesic) for the prevention, treatment, or amelioration of pain (particularly hyperalgesia) caused as a result of inflammatory disease, or as a result of combined inflammatory, autoimmune and neuropathic tissue damage, including rheumatoid arthritis, osteoarthritis, rheumatoid spondylitis, gouty arthritis, and other arthritic conditions, cancer, HIV, Chronic Obstructive Pulmonary Disease (COPD), acute bronchitis, chronic bronchitis, emphysema, bronchiectasis, cystic fibrosis, pneumonia, pleurisy, acute asthma, chronic asthma, acute respiratory distress syndrome, adult respiratory distress syndrome (ARDS), infant respiratory distress syndrome (IRDS) acute lung injury (ALI), laryngitis, pharangitis, persistent asthma, chronic asthmatic bronchitis, interstitial lung disease, lung malignancies, alpha-anti-trypsin deficiency, bronchiolitis obliterans, sarcoidosis, pulmonary fibrosis, collagen vascular disorders, allergic rhinitis, nasal congestion, status asthmaticus, smoking related pulmonary disease, pulmonary hypertension, pulmonary oedema, pulmonary embolism, pleural effusion, pneumothorax, haemothorax, lung cancer, allergies, pollinosis Hay fever), sneeze, vasomotor rhinitis, mucositis, sinusitis, exogenous irritant induced illness ($SO_2$, smog, pollution), airway hypersensitivity, milk product intolerance, Luffer's pneumonia, pneumoconiosis, collagen induced vascular disease, granulomatous disease, bronchial inflammation, chronic pulmonary inflammatory disease, bone resorption diseases, reperfusion injury (including damage caused to organs as a consequence of reperfusion following ischaemic episodes e.g. myocardial infarcts, strokes), autoimmune damage (including multiple sclerosis, Guillam Barre Syndrome, myasthenia gravis) graft v. host rejection, allograft rejections, fever and myalgia due to infection, AIDS related complex (ARC), keloid formation, scar tissue formation, Crohn's disease, ulcerative colitis and pyresis, irritable bowel syndrome, osteoporosis, cerebral malaria and bacterial meningitis, bowel pain, cancer pain, back pain, fibromyalgia, post-operative pain; or in any of the above pathological conditions where bacterial or viral infection is a cause or exacerbates the condition.

According to the invention there is also provided use of a compound of formula (I) for the prevention, treatment, or amelioration of ischaemic pain. The term "ischaemic pain" is used herein to mean pain associated with a reduction in blood supply to a part of the body. A reduced blood supply limits the supply of oxygen (hypoxia) and energy to that part of the body. Ischaemia arises from poor blood perfusion of tissues and so ischaemic pain arises in coronary artery disease, peripheral artery disease, and conditions which are characterized by insufficient blood flow, usually secondary to atherosclerosis. Other vascular disorders can also result in ischaemic pain. These include: left ventricular hypertrophy, coronary artery disease, essential hypertension, acute hypertensive emergency, cardiomyopathy, heart insufficiency, exercise tolerance, chronic heart failure, arrhythmia, cardiac dysrhythmia, syncopy, arteriosclerosis, mild chronic heart failure, angina pectoris, Prinzmetal's (variant) angina, stable angina, and exercise induced angina, cardiac bypass reocclusion, intermittent claudication (arteriosclerosis oblitterens), arteritis, diastolic dysfunction and systolic dysfunction, atherosclerosis, post ischaemia/reperfusion injury, diabetes (both Types I and II), thromboembolisms. Haemorrhagic accidents can also result in ischaemic pain. In addition poor perfusion can result in neuropathic and inflammatory pain arising from hypoxia-induced nerve cell damage (e.g. in cardiac arrest or bypass operation, diabetes or neonatal distress); or in any of the above pathological conditions where bacterial or viral infection is a cause or exacerbates the condition.

There is further provided according to the invention use of a compound of formula (I) for the manufacture of a medicament for the prevention, treatment, or amelioration of inflammation. There is further provided according to the invention a method of prevention, treatment, or amelioration of inflammation, which comprises administering a compound of formula (I) to a subject in need of such prevention, treatment, or amelioration.

In particular, it is believed that compounds of formula (I) can be used to prevent, treat, or ameliorate inflammation caused by, or associated with: cancer (such as leukemias, lymphomas, carcinomas, colon cancer, breast cancer, lung cancer, pancreatic cancer, hepatocellular carcinoma, kidney cancer, melanoma, hepatic, lung, breast, and prostate metastases, etc.); auto-immune disease (such as organ transplant rejection, lupus erythematosus, graft v. host rejection, allograft rejections, multiple sclerosis, rheumatoid arthritis, type I diabetes mellitus including the destruction of pancreatic islets leading to diabetes and the inflammatory consequences of diabetes); autoimmune damage (including multiple sclerosis, Guillam Barre Syndrome, myasthenia gravis); obesity; cardiovascular conditions associated with poor tissue perfusion and inflammation (such as atheromas, atherosclerosis, stroke, ischaemia-reperfusion injury, claudication, spinal cord injury, congestive heart failure, vasculitis, haemorrhagic shock, vasospasm following subarachnoid haemorrhage, vasospasm following cerebrovascular accident, pleuritis, pericarditis, the cardiovascular complications of diabetes); ischaemia-reperfusion injury, ischaemia and associated inflammation, restenosis following angioplasty and inflammatory aneurysms; epilepsy, neurodegeneration (including Alzheimer's Disease), muscle fatigue or muscle cramp (particularly athletes' cramp), arthritis (such as rheumatoid arthritis, osteoarthritis, rheumatoid spondylitis, gouty arthritis), fibrosis (for example of the lung, skin and liver), multiple sclerosis, sepsis, septic shock, encephalitis, infectious arthritis, Jarisch-Herxheimer reaction, shingles, toxic shock, cerebral malaria, Lyme's disease, endotoxic shock, gram negative shock, haemorrhagic shock, hepatitis (arising both from tissue damage or viral infection), deep vein thrombosis, gout; conditions associated with breathing difficulties (e.g. impeded and obstructed airways, bronchoconstriction, pulmonary vasoconstriction, impeded respiration, silicosis, pulmonary sarcosis, pulmonary hypertension, pulmonary vasoconstriction, bronchial allergy and vernal conjunctivitis); conditions associated with inflammation of the skin (including psoriasis, eczema, ulcers, contact dermatitis); conditions associated with inflammation of the bowel (including Crohn's disease, ulcerative colitis and pyresis, irritable bowel syndrome, inflammatory bowel disease); HIV (particularly HIV infection), cerebral malaria, bacterial meningitis, TNF-enhanced HIV replication, TNF inhibition of AZT and DDI activity, osteoporosis and other bone resorption diseases, osteoarthritis, rheumatoid arthritis, infertility from endometriosis, fever and myalgia due to infection, cachexia secondary to cancer, cachexia secondary to infection or malignancy, cachexia secondary to acquired immune deficiency syndrome (AIDS), AIDS related complex (ARC), keloid formation, scar tissue formation, adverse effects from amphotericin B treatment, adverse effects from interleukin-2 treatment, adverse effects from OKT3 treatment, or adverse effects from GM-CSF treatment, and other conditions mediated by excessive anti-inflammatory cell (including neutrophil, eosinophil, macrophage and T-cell) activity; or in any of the above pathological conditions where bacterial or viral infection is a cause or exacerbates the condition.

Continuous low grade inflammation is known to be associated with obesity (in the presence or absence of insulin resistance and Type II diabetes) (Browning et al (2004) Metabolism 53, 899-903, Inflammatory markers elevated in blood of obese women; Mangge et al. (2004) Exp Clin Endocrinol Diabetes 112, 378-382, Juvenile obesity correlates with serum inflammatory marker C-reactive protein; Maachi et al., Int J Obes Relat Metab Disord. 2004 28, 993-997, Systemic low grade inflammation in obese people). A possible reason for this is that fat cells secrete TNF alpha and interleukins 1 and 6, which are pro-inflammatory.

Compounds of the invention that are selective agonists of adenosine A2A receptors are particularly preferred because it is believed that such compounds will have strong anti-inflammatory activity. By selective agonists of adenosine A2A receptors is meant agonists that activate adenosine A2A receptors at concentrations that are lower (preferably one thousandth to one fifth) than required to activate adenosine A1 receptors. Furthermore, A1 receptors have pro-inflammatory activity, so such effects are expected to be minimised for compounds that are selective for A2A receptors.

Compounds of formula (I) are believed to be much more effective at low doses than other adenosine receptor agonists. Thus, it is expected that compounds of the invention can be effectively administered at doses at which they have reduced probability and severity of side effects, or at which side effects are not observed. Such compounds provide significant advantages over other adenosine receptor agonists which only have anti-inflammatory effects at the same concentrations at which serious side effects are observed.

It is also believed that compounds of formula (I) may be effective as disease-modifying anti-rheumatic drugs (DMARDs), in particular for use in the prevention, treatment, or amelioration of rheumatoid arthritis, and possibly other arthropathies such as osteoarthritis.

Medications used to treat rheumatoid arthritis (RA) can be divided into two groups: those that help relieve RA symptoms; and those that help modify the disease. Drugs that help to relieve RA symptoms include nonsteroidal anti-inflammatory drugs (NSAIDs) that relieve pain and reduce inflammation in the affected joints, analgesics (such as acetaminophen and narcotic pain medications) that relieve pain but do not slow joint damage or reduce inflammation, and corticosteroids that are anti-inflammatory drugs.

DMARDs help to improve RA symptoms (such as joint swelling and tenderness), but also slow the progression of joint damage caused by RA. Thus, while there is no cure for RA, DMARDs help to slow the progression of RA. In the past DMARDs were usually used to treat RA after NSAID therapy failed. However, DMARDs are now beginning to be used earlier in the course of RA because studies have suggested that early intervention with DMARDs offers important benefits. DMARDs and NSAIDs are often used in combination with each other.

Results from clinical studies have shown that known DMARDs slow the progression of RA. After 6 months of treatment, the rate of bone and cartilage damage had already started to slow in patients' joints. After 1 year, patients showed very little progression of joint damage, and after 2 years X rays showed that few patients in the study had newly damaged joints during the second year of treatment.

Examples of known DMARDs include sulphasalazine, penicillamine, chloroquine, hydroxychloroquine, gold (by intramuscular injection or orally as auranofin), methotrexate, cyclosporin, azathioprine, cyclophosphamide, leflunomide. More recently biological DMARDs have been developed which inhibit tumour necrosis factor alpha (TNF alpha). One example is Humira® which is indicated for reducing signs and symptoms and inhibiting the progression of structural damage in adults with moderately to severely active RA who have had an inadequate response to one or more DMARDs. Humira® is an anti-TNF alpha antibody.

Many of the known DMARDs cause serious side effects. Consequently, it is desired to provide new DMARDs that can be administered with minimal side effects.

WO 2005/084653 shows the ability of spongosine to reduce phorbol ester induced TNF alpha release in U937 human macrophage cells. On this basis, it is believed that spongosine and related compounds of the invention also have DMARD activity.

According to the invention there is provided use of a compound of formula (I) in the manufacture of a medicament for slowing the progression of arthropathy. There is also provided according to the invention a method of slowing the progression of arthropathy, which comprises administering a compound of formula (I) to a subject in need thereof.

Preferably the progression of RA is slowed, and in particular the progression of joint damage caused by RA. A compound of the invention may be administered to the subject at any stage in the course of RA. A compound of the invention may be administered in combination with one or more NSAIDs or other DMARDs.

Compounds of the invention are believed to be effective as DMARDs even when administered at doses expected to give plasma concentrations well below those known to activate adenosine receptors. At these doses, it is believed that the compounds do not cause the significant side effects associated with administration of higher doses of spongosine, or other adenosine receptor agonists.

A particular advantage of use of compounds of the invention as DMARDs is that it is believed that they will be orally active, in contrast to anti-TNF alpha antibodies which must be injected.

It has also been appreciated that compounds of formula (I) may be effective in preventing, treating, or ameliorating macro and micro vascular complications of type 1 or 2 diabetes (including retinopathy, nephropathy, autonomic neuropathy), or blood vessel damage caused by ischaemia (either diabetic or otherwise) or atherosclerosis (either diabetic or otherwise).

According to the invention, there is provided use of a compound of formula (I) in the manufacture of a medicament for the prevention, treatment, or amelioration of macro or micro vascular complications of type 1 or 2 diabetes, retinopathy, nephropathy, autonomic neuropathy, or blood vessel damage caused by ischaemia or atherosclerosis. According to the invention there is also provided a method of preventing, treating, or ameliorating macro or micro vascular complications of type 1 or 2 diabetes, retinopathy, nephropathy, autonomic neuropathy, or blood vessel damage caused by ischaemia or atherosclerosis, in a subject in need of such prevention, treatment, or amelioration, which comprises administering a compound of formula (I) to the subject.

Compounds of formula (I) are believed to be effective in prevention, treatment, or amelioration of macro or micro vascular complications of type 1 and 2 diabetes, including retinopathy, nephropathy, autonomic neuropathy, or blood vessel damage caused by ischaemia or atherosclerosis (either diabetic or otherwise) even when administered at doses expected to give plasma concentrations well below those known to activate adenosine receptors. At these doses, it is believed that the compounds do not cause the significant side effects associated with administration of higher doses of spongosine, or other adenosine receptor agonists.

Compounds of formula (I) are also believed to be effective in the promotion of wound healing. According to the invention there is provided use of a compound of formula (I) in the manufacture of a medicament for the promotion of wound healing. There is also provided according to the invention a method of promoting wound healing in a subject, which comprises administering a compound of formula (I) to the subject.

The amount of a compound of formula (I) that is administered to a subject is preferably an amount which gives rise to a peak plasma concentration of the compound that is less than the EC50 value of the compound at adenosine receptors (preferably at pH 7.4).

Thus, preferably the amount of a compound of the invention that is administered to a subject should be an amount which gives rise to a peak plasma concentration that is less than the EC50 value of the compound at adenosine receptors. Preferably the peak plasma concentration of the compound is one ten thousandth to one half (or one ten thousandth to one fifth, or one ten thousandth to one twentieth, or one ten thousandth to one hundredth, or one ten thousandth to one thousandth, or one thousandth to one half, or one thousandth to one fifth, or one thousandth to one twentieth, or one fiftieth to one tenth, or one hundredth to one half, or one hundredth to one fifth, or one fiftieth to one third, or one fiftieth to one half, or one fiftieth to one fifth, or one tenth to one half, or one tenth to one fifth) of the EC50 value.

Preferably the amount of a compound of the invention that is administered gives rise to a plasma concentration that is maintained for more than one hour at one ten thousandth to one half (or one ten thousandth to one fifth, or one ten thousandth to one twentieth, or one ten thousandth to one hundredth, or one ten thousandth to one thousandth, or one thousandth to one half, or one thousandth to one fifth, or one thousandth to one twentieth, or one fiftieth to one tenth, or one hundredth to one half, or one hundredth to one fifth, or one fiftieth to one half, or one fiftieth to one fifth, or one tenth to one half, or one tenth to one fifth) of the EC50 value of the compound at adenosine receptors.

For the avoidance of doubt, the EC50 value of a compound is defined herein as the concentration of the compound that provokes a receptor response halfway between the baseline receptor response and the maximum receptor response (as determined, for example, using a dose-response curve).

The EC50 value should be determined under standard conditions (balanced salt solutions buffered to pH 7.4). For EC50 determinations using isolated membranes, cells and tissues this would be in buffered salt solution at pH 7.4 (e.g. cell culture medium), for example as in Daly et al., Pharmacol. (1993) 46, 91-100), or preferably as in Tilburg et al (J. Med. Chem. (2002) 45, 91-100). The EC50 could also be determined in vivo by measuring adenosine receptor mediated responses in a normal healthy animal, or even in a tissue perfused under normal conditions (i.e. oxygenated blood, or oxygenated isotonic media, also buffered at pH 7.4) in a normal healthy animal.

It will be appreciated that the EC50 value of the compound is likely to be different for different adenosine receptors (i.e. the A1, A2A, A2B, A3 adenosine receptors). The amount of the compound that is to be administered should be calculated relative to the lowest EC50 value of the compound at the different receptors.

Alternatively, the amount of a compound of the invention that is administered may be an amount that gives rise to a peak plasma concentration that is less than the lowest Kd value of the compound at adenosine receptors (i.e. less than the lowest Kd value of the compound at A1, A2A, A2B, and A3 adenosine receptors). Preferably the peak plasma concentration of the compound is one ten thousandth to one half (or one ten thousandth to one fifth, or one ten thousandth to one twentieth, or one ten thousandth to one hundredth, or one ten thousandth to one thousandth, or one thousandth to one half, or one thousandth to one third, or one thousandth to one fifth, or one thousandth to one twentieth, or one fiftieth to one tenth, or one hundredth to one half, or one hundredth to one fifth, or one fiftieth to one half, or one fiftieth to one fifth, or one tenth to one half, or one tenth to one fifth) of the lowest Kd value.

Preferably the amount of the compound that is administered is an amount that gives rise to a plasma concentration that is maintained for more than one hour at one ten thousandth to one half (or one ten thousandth to one fifth, or one ten thousandth to one twentieth, or one ten thousandth to one hundredth, or one ten thousandth to one thousandth, or one thousandth to one half, or one thousandth to one fifth, or one thousandth to one twentieth, or one fiftieth to one tenth, or one hundredth to one half, or one hundredth to one fifth, or one fiftieth to one half, or one fiftieth to one fifth, or one fiftieth to one third, or one tenth to one half, or one tenth to one fifth) of the lowest Kd value of the compound at adenosine receptors.

The Kd value of the compound at each receptor should be determined under standard conditions using plasma membranes as a source of the adenosine receptors derived either from tissues or cells endogenously expressing these receptors or from cells transfected with DNA vectors encoding the adenosine receptor genes. Alternatively whole cell preparations using cells expressing adenosine receptors can be used. Labelled ligands (e.g. radiolabelled) selective for the different receptors should be used in buffered (pH 7.4) salt solutions (see e.g. Tilburg et al, J. Med. Chem. (2002) 45, 420-429) to determine the binding affinity and thus the Kd of the compound at each receptor.

Alternatively, the amount of a compound of the invention that is administered may be an amount that is one ten thousandth to one half (or one ten thousandth to one fifth, or one ten thousandth to one twentieth, or one ten thousandth to one hundredth, or one ten thousandth to one thousandth, or one thousandth to one half, or one thousandth to one fifth, or one thousandth to one twentieth, or one fiftieth to one tenth, or one hundredth to one half, or one hundredth to one fifth, or one fiftieth to one half, or one fiftieth to one third, or one fiftieth to one fifth, or one tenth to one half, or one tenth to one fifth) of the minimum amount of the compound that gives rise to bradycardia, hypotension or tachycardia side effects in animals of the same species as the subject to which the compound is to be administered.

Preferably the amount administered gives rise to a plasma concentration that is maintained for more than one hour at one ten thousandth to one half (or one ten thousandth to one fifth, or one ten thousandth to one twentieth, or one ten thousandth to one hundredth, or one ten thousandth to one thousandth, or one thousandth to one half, or one thousandth to one fifth, or one thousandth to one twentieth, or one fiftieth to one tenth, or one hundredth to one half, or one hundredth to one fifth, or one fiftieth to one half, or one fiftieth to one fifth, or one tenth to one half, or one tenth to one fifth) of the minimum plasma concentration of the compound that gives rise to the side effects.

The appropriate dosage of a compound of the invention will vary with the age, sex, weight, and condition of the subject being treated, the potency of the compound (such as its EC50 value for an adenosine receptor), its half life, its absorption by the body, and the route of administration, etc. However, the appropriate dosage can readily be determined by one skilled in the art.

A suitable way to determine the appropriate dosage is to assess cardiovascular changes (for example by ecg and blood pressure monitoring) at or around the EC50 value of the compound for an adenosine receptor (preferably the receptor for which it has highest affinity) to determine the maximum tolerated dose. The therapeutically effective dose is then expected to be one ten thousandth to one half (or one ten thousandth to one fifth, or one ten thousandth to one twentieth, or one ten thousandth to one hundredth, or one ten thousandth to one thousandth, or one thousandth to one half, or one thousandth to one fifth, or one thousandth to one twentieth, or one fiftieth to one tenth, or one hundredth to one half, or one hundredth to one fifth, or one fiftieth to one half, or one fiftieth to one third, or one fiftieth to one fifth, or one tenth to one half, or one tenth to one fifth) of the maximum tolerated dose.

Example 23 below shows how a suitable dosage range for compounds of the invention may be determined. Spongosine is the compound used in this example, but it will be appreciated that similar methods may be used for compounds of the invention. The preferred dosage of spongosine was determined to be less than 28 mg in humans. This dosage gives rise to plasma concentrations between 0.5 and 0.9 $\mu$M (close to the Kd at adenosine A2A receptors at pH 7.4). Based on this result, a preferred dosage range for spongosine is 0.03 to 0.3 mg/kg.

The minimum plasma concentration of spongosine giving maximal analgesic relief in a rat adjuvant model of arthritis was 0.06 $\mu$M, considerably less than the EC50 of spongosine at the adenosine A2A receptor which is approximately 1 $\mu$M. Preferred dosing levels in humans give maximum plasma concentrations between 0.005 and 0.5 $\mu$M which are significantly lower than those expected to provide an analgesic or an anti-inflammatory effect by an action on this receptor.

Alternatively, appropriate therapeutic concentrations of compounds of the invention are expected to be approximately 10-20 times the Ki for an adenosine receptor (the receptor for which the compound has the highest affinity) at pH 5.5.

It is expected that the amount of a compound of the invention that is administered should be 0.001-15 mg/kg. The amount may be up to 10, 5, 2, 1, 0.5, 0.2, 0.1, or 0.01 mg/kg. The amount may be at least 0.001, 0.01, 0.1, 0.2, 0.5, 1, 2, 5, or 10 mg/kg. Preferred ranges are 0.001-10, 0.001-5, 0.001-2, 0.001-1, 0.001-0.1, 0.001-0.01, 0.01-15, 0.01-10, 0.01-5, 0.01-2, 0.01-1, 0.1-10, 0.1-5, 0.1-2, 0.1-1, 0.1-0.5, 0.1-0.4, 0.2-15, 0.2-10, 0.2-5, 0.2-2, 0.2-1.2, 0.2-1, 0.6-1.2 mg/kg.

Preferred doses for a human subject (for example a 70 kg subject) are less than 420 mg, preferably less than 28 mg, more preferably less than 21 mg, and preferably at least 0.07, 0.1, 0.7, or 0.8 mg, more preferably at least 3.5 or 7 mg. More preferably 7-70 mg, 14-70 mg, or 3.5-21 mg.

It is believed that the dosage amounts specified above are significantly lower (up to approximately 1000 times lower) than would be expected to be required for an analgesic or an anti-inflammatory effect based on the EC50 value of the compound at the adenosine A2A receptor.

Particularly preferred dosage amounts give rise to plasma concentrations that are approximately one hundredth to one half of the EC50 value of the compound at the adenosine receptor for which it has highest affinity.

A compound of the invention may be administered with or without other therapeutic agents, for example analgesics, anti-hyperalgesics (such as gabapentin, pregabalin, cannabinoids, sodium or calcium channel modulators, anti-epileptics or anti-depressants) anti-inflammatories (such as opiates, steroids, NSAIDs, cannabinoids, tachykinin modulators, or bradykinin modulators), DMARDs, or anti-pathogenic agents.

In general, a compound of the invention may be administered by known means, in any suitable formulation, by any suitable route. A compound of the invention is preferably administered orally, parenterally, sublingually, transdermally, intrathecally, or transmucosally. Other suitable routes include intravenous, intramuscular, subcutaneous, inhaled, and topical. The amount of drug administered will typically be higher when administered orally than when administered, say, intravenously.

It will be appreciated that a compound of the invention may be administered together with a physiologically acceptable carrier, excipient, or diluent.

To maintain therapeutically effective plasma concentrations for extended periods of time, compounds of the invention may be incorporated into slow release formulations.

Suitable compositions, for example for oral administration, include solid unit dose forms, and those containing liquid, e.g. for injection, such as tablets, capsules, vials and ampoules, in which the active agent is formulated, by known means, with a physiologically acceptable excipient, diluent or carrier. Suitable diluents and carriers are known, and include, for example, lactose and talc, together with appropriate binding agents etc.

A unit dosage of a compound of formula (I) typically comprises up to 500 mg (for example 1-500 mg, or 5-500 mg) of the active agent. Preferably the active agent is in the form of a pharmaceutical composition comprising the active agent and a physiologically acceptable carrier, excipient, or diluent. Preferred amounts of the active ingredient in a unit dose are 0.001-10, 0.001-5, 0.001-2, 0.001-1, 0.001-0.1, 0.001-0.01, 0.01-15, 0.01-10, 0.01-5, 0.01-2, 0.01-1, 0.1-10, 0.1-5, 0.1-2, 0.1-1, 0.1-0.5, 0.1-0.4, 0.2-15, 0.2-10, 0.2-5, 0.2-2, 0.2-1.2, 0.2-1, 0.5 to 1, 0.6-1.2, typically about 0.2 or 0.6 mg of the active agent per kg of the subject. Preferred amounts of the active agent are less than 420 mg, preferably less than 28 mg, more preferably less than 21 mg, and preferably at least 0.07, 0.1, 0.7 or 0.8 mg, more preferably at least 3.5 or 7 mg. More preferably 7 to 70 mg, or 14 to 70 mg, 3.5 to 21 mg, 0.07-0.7 mg, or 0.7-7 mg. At these levels, it is believed that effective treatment can be achieved substantially without a concomitant fall (for example, no more than 10%) in blood pressure and/or increase in compensatory heart rate.

A unit dosage of a compound of the invention may further comprise one or more other therapeutic agents, for example analgesics, anti-hyperalgesics, anti-inflammatories, DMARDs, or anti-pathogenic agents.

Preferably a compound of the invention is administered once per day, although the compound may be administered at a frequency of two or three times per day if desired.

Compounds of the invention can also serve as a basis for identifying more effective drugs, or drugs that have further reduced side effects.

Examples of pharmaceutically acceptable salts are organic addition salts formed with acids which form a physiologically acceptable anion, for example, tosylate, methanesulphonate, malate, acetate, citrate, malonate, tartarate, succinate, benzoate, ascorbate, $\alpha$-ketoglutarate, and $\alpha$-glycerophosphate. Suitable inorganic salts may also be formed, including hydrochloride, sulphate, nitrate, bicarbonate, and carbonate salts.

Pharmaceutically acceptable salts may be obtained using standard procedures well known in the art, for example by reacting a sufficiently basic compound such as an amine with a suitable acid affording a physiologically acceptable anion.

Alkali metal (for example, sodium, potassium, or lithium) or alkaline earth metal (for example calcium) salts of carboxylic acids can also be made.

The recitation of a listing of chemical groups in any definition of a variable herein includes definitions of that variable as any single group or combination of listed groups. The recitation of an embodiment for a variable herein includes that embodiment as any single embodiment or in combination with any other embodiments or portions thereof.

There is also provided according to the invention methods of synthesis of compound numbers 1-21 as defined in Example 1 below.

According to the invention there is provided a method of producing a compound of any of formulae 1-7 as defined in Example 1, which comprises reacting a compound of the following general formula (A) with a base and: (i) CF$_3$CF$_2$CH$_2$OH; (ii) 3-(4-(trifluoromethyl)phenyl)phenol; (iii) 3,4-dichlorophenol; (iv) 3-trifluoromethyl, 4-fluorophenol; (v) 3-trifluoromethyl, 4-chlorophenol; (vi) 3-chloro, 4-cyanophenol; or (vii) 3,5-bis(trifluoromethyl)phenol; and de-protecting the reaction product to produce the compound of formula 1-7:

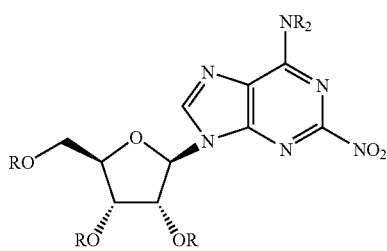

(A)

wherein each R is independently a protecting group.

A preferred solvent is a non-alcohol solvent. Suitable examples are tetrahydrofuran (THF), dimethyl formamide (DMF) and acetonitrile. THF is preferred.

Suitable bases are sodium hydride, potassium tert-butoxide, butyllithium and lithium hexamethyldisilazide (LHMDS). Sodium hydride is the preferred base for synthesising compound 1 and potassium tert-butoxide is the preferred base for synthesising compounds 2-7.

Preferred protecting groups are carboxylic acid-derived acyl groups which may be aliphatic, aromatic, heterocyclic, saturated or unsaturated. Examples of suitable protecting groups are acetyl, propionyl, caproyl, palmitoyl, benzoyl, toluoyl, furoyl, sulfonyl, isopropylidene, alkoxyalkylidene. Most preferably, the protecting groups are acetyl or benzoyl. Alternatively, a silicon-based protecting group e.g. trimethylsilyl (TMS) or tert-butyldimethylsilyl (TBDMS) may be used.

De-protection of the reaction product may be carried out using standard techniques, for example, using sodium methoxide in methanol, or heating with ammonia. Where isopropylidene or alkoxyalkylidene are used as protecting groups, an acid such as trifluoroacetic acid (TFA) will be required for removal of the protecting groups. Silicon-based protecting groups may be removed with tetrabutylammonium fluoride (TBAF), or an acid such TFA.

There is also provided according to the invention a method of producing a compound of formula 8 as defined in Example 1, which comprises reacting 2-chloro adenosine with 4-(3,4-dichlorophenyl)piperazine to produce the compound of formula 8, or reacting a compound of the following general formula with 4-(3,4-dichlorophenyl)piperazine, and de-protecting the reaction product to produce the compound of formula 8:

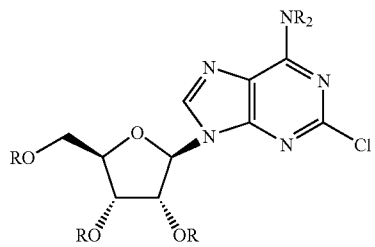

wherein each R is independently a protecting group as defined above.

A preferred solvent is an organic solvent, such as DMF, methanol, or ethanol. The 4-(3,4-dichlorophenyl)piperazine may act as a solvent if desired. Alternatively, water may be used as solvent.

Preferably the reaction is heated to 100-200° C.

De-protection may be carried out as described above.

There is also provided according to the invention a method of producing a compound of any of formulae 9-13 as defined in Example 1, which comprises reacting 2-iodo adenosine with: (i) 3,4-dichlorophenylboronic acid; (ii) 3,5-difluorophenylboronic acid; (iii) 3,5-bis(trifluoromethyl)phenylboronic acid; (iv) 3,4,5-trifluorophenylboronic acid; or (v) 2-benzofuranylboronic acid, to produce the compound of formula 9-13, or reacting a compound of the following general formula (B) with: (i) 3,4-dichlorophenylboronic acid; (ii) 3,5-difluorophenylboronic acid; (iii) 3,5-bis(trifluoromethyl) phenylboronic acid; (iv) 3,4,5-trifluorophenylboronic acid; or (v) 2-benzofuranylboronic acid, and de-protecting the reaction product to produce the compound of formula 9-13:

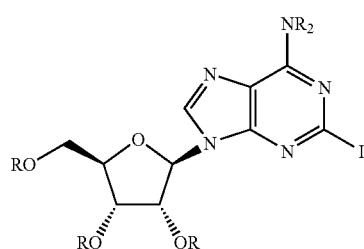

(B)

wherein each R is independently a protecting group as defined above.

Preferably the reaction is heated to 100-200° C.

A preferred solvent is an organic solvent, preferably an alcohol, toluene, ethyl acetate or DMF (or a combination thereof).

Preferably the reaction is carried out in the presence of a base, such as cesium carbonate, potassium carbonate, potassium hydroxide or sodium carbonate.

A palladium catalyst is preferably used, such as Pd(PPh$_3$)$_4$, Pd$_2$(dba)$_2$, Pd$_2$Cl$_2$(PPh$_3$)$_2$ or Pd(OAc)$_2$.

De-protection may be carried out as described above.

According to the invention there is also provided a method of producing a compound of formula 14 as defined in Example 1, which comprises de-protecting and methoxylating a compound of the following general formula (C) to produce the compound of formula 14:

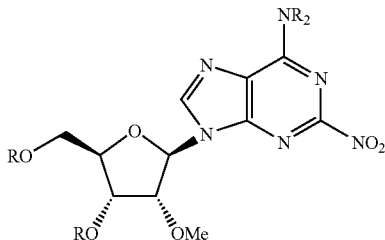

(C)

wherein each R is independently a protecting group.

Preferred protecting groups are carboxylic acid-derived acyl groups which may be aliphatic, aromatic, heterocyclic, saturated or unsaturated. Examples of suitable protecting groups are acetyl, propionyl, caproyl, palmitoyl, benzoyl, toluoyl, furoyl, or sulfonyl. Most preferably, the protecting groups are acetyl or benzoyl. Alternatively, a silicon-based protecting group may be used.

De-protection may be carried out as described above.

Methoxylation may be carried out using standard techniques, for example, using sodium methoxide in methanol. Alternatively, potassium methoxide may be used.

The preferred solvent is methanol.

It will be appreciated that methoxylation and de-protection may occur at substantially the same time. Alternatively, methoxylation could take place before de-protection.

According to the invention there is also provided a method of producing a compound of any of formulae 15-18 as defined in Example 1, which comprises reacting a compound of general formula (C) with a base and: (i) $CHF_2CH_2OH$; (ii) cyclopentanemethanol; (iii) 2,5-difluorophenol; or (iv) (S)-sec-butylamine; and de-protecting the reaction product to produce the compound of formula 15-18.

Preferred protecting groups are as described above for methods of producing a compound of formula 14.

A preferred solvent is THF, although where (S)-sec-butylamine is a reactant this may act as the solvent.

Sodium hydride is the preferred base for synthesising compounds 15-16 and potassium tert-butoxide is the preferred base for synthesising compound 17.

De-protection may be carried out as described above.

There is also provided according to the invention a method of producing a compound of formula 19 or 20 as defined in Example 1, which comprises reacting a compound of the following general formula (D) with: (i) n-hexylamine; or (ii) cyclopentylamine; and de-protecting the reaction product to produce the compound of formula 19 or 20:

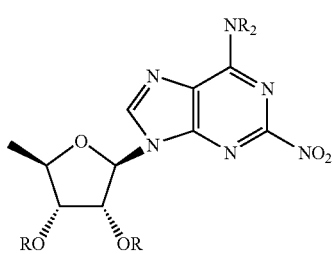

(D)

wherein each R is independently a protecting group.

Preferred protecting groups are as described above for formula (A).

A preferred solvent is THF, although if desired the n-hexylamine or cyclopentylamine could act as a solvent.

De-protection may be carried out as described above.

According to the invention there is further provided a method of producing a compound of formula 21 as defined in Example 1, which comprises reacting a compound of the following general formula (E) with cyclopentylamine and de-protecting the reaction product to produce the compound of formula 21:

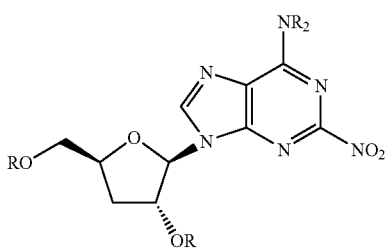

(E)

wherein each R is independently a protecting group.

Preferred protecting groups are as described above for formula (C).

A preferred solvent is THF, although if desired the cyclopentylamine could act as a solvent.

De-protection may be carried out as described above.

Preferably, methods of the invention for producing compounds of formulae 1-21 comprise the steps shown in Schemes 1-21 (found in Examples 2-22 below), respectively. Particularly preferred methods of producing compounds of formulae 1-21 are as described in Examples 2-22 below, and as follows:

A method of producing a compound of formula 1 as defined in Example 1, which comprises reacting a compound of the following general formula (A) with CF3CF2CH2OH and a base, and de-protecting the reaction product to produce the compound of formula 1:

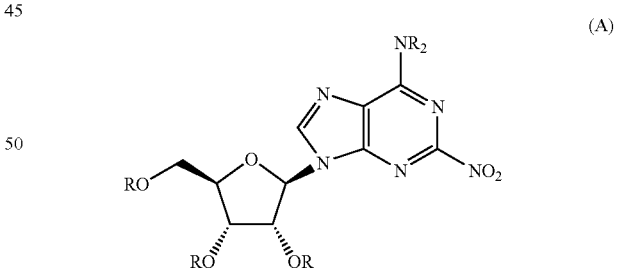

(A)

wherein each R is independently a protecting group.

A method of producing a compound of formula 2 as defined in Example 1, which comprises reacting a compound of general formula (A) with 3-(4-(trifluoromethyl)phenyl) phenol and a base, and de-protecting the reaction product to produce the compound of formula 2.

A method of producing a compound of formula 3 as defined in Example 1, which comprises reacting a compound of general formula (A) with 3,4-dichlorophenol and a base, and de-protecting the reaction product to produce the compound of formula 3.

A method of producing a compound of formula 4 as defined in Example 1, which comprises reacting a compound of general formula (A) with 3-trifluoromethyl, 4-fluorophenol and a base, and de-protecting the reaction product to produce the compound of formula 4.

A method of producing a compound of formula 5 as defined in Example 1, which comprises reacting a compound of general formula (A) with 3-trifluoromethyl, 4-chlorophenol and a base, and de-protecting the reaction product to produce the compound of formula 5.

A method of producing a compound of formula 6 as defined in Example 1, which comprises reacting a compound of general formula (A) with 3-chloro, 4-cyanophenol and a base, and de-protecting the reaction product to produce the compound of formula 6.

A method of producing a compound of formula 7 as defined in Example 1, which comprises reacting a compound of general formula (A) with 3,5-bis(trifluoromethyl)phenol and a base, and de-protecting the reaction product to produce the compound of formula 7.

A method of producing a compound of formula 8 as defined in Example 1, which comprises reacting 2-chloro adenosine with 4-(3,4-dichlorophenyl)piperazine to produce the compound of formula 8, or reacting a compound of the following general formula with 4-(3,4-dichlorophenyl)piperazine, and de-protecting the reaction product to produce the compound of formula 8:

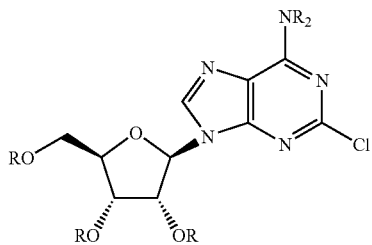

wherein each R is independently a protecting group.

A method of producing a compound of formula 9 as defined in Example 1, which comprises reacting 2-iodo adenosine with 3,4-dichlorophenylboronic acid to produce the compound of formula 9, or reacting a compound of the following general formula (B) with 3,4-dichlorophenylboronic acid, and de-protecting the reaction product to produce the compound of formula 9:

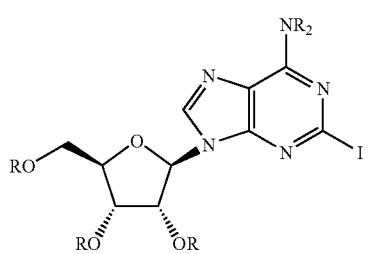

(B)

wherein each R is independently a protecting group.

A method of producing a compound of formula 10 as defined in Example 1, which comprises reacting 2-iodo adenosine with 3,5-difluorophenylboronic acid to produce the compound of formula 10, or reacting a compound of general formula (B) with 3,5-difluorophenylboronic acid, and de-protecting the reaction product to produce the compound of formula 10.

A method of producing a compound of formula 11 as defined in Example 1, which comprises reacting 2-iodo adenosine with 3,5-bis(trifluoromethyl)phenylboronic acid to produce the compound of formula 11, or reacting a compound of general formula (B) with 3,5-bis(trifluoromethyl)phenylboronic acid, and de-protecting the reaction product to produce the compound of formula 11.

A method of producing a compound of formula 12 as defined in Example 1, which comprises reacting 2-iodo adenosine with 3,4,5-trifluorophenylboronic acid to produce the compound of formula 12, or reacting a compound of general formula (B) with 3,4,5-trifluorophenylboronic acid, and de-protecting the reaction product to produce the compound of formula 12.

A method of producing a compound of formula 13 as defined in Example 1, which comprises reacting 2-iodo adenosine with 2-benzofuranylboronic acid to produce the compound of formula 13, or reacting a compound of general formula (B) with 2-benzofuranylboronic acid, and de-protecting the reaction product to produce the compound of formula 13.

A method of producing a compound of formula 14 as defined in Example 1, which comprises de-protecting and methoxylating a compound of the following general formula (C) to produce the compound of formula 14:

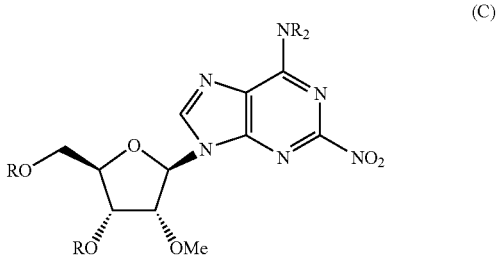

(C)

wherein each R is independently a protecting group.

A method of producing a compound of formula 15 as defined in Example 1, which comprises reacting a compound of general formula (C) with CHF2CH2OH and a base, and de-protecting the reaction product to produce the compound of formula 15.

A method of producing a compound of formula 16 as defined in Example 1, which comprises reacting a compound of general formula (C) with cyclopentanemethanol and a base, and de-protecting the reaction product to produce the compound of formula 16.

A method of producing a compound of formula 17 as defined in Example 1, which comprises reacting a compound of general formula (C) with 2,5-difluorophenol and a base, and de-protecting the reaction product to produce the compound of formula 17.

A method of producing a compound of formula 18 as defined in Example 1, which comprises reacting a compound of general formula (C) with (S)-sec-butylamine and a base, and de-protecting the reaction product to produce the compound of formula 18.

A method of producing a compound of formula 19 as defined in Example 1, which comprises reacting a compound of the following general formula (D) with n-hexylamine and de-protecting the reaction product to produce the compound of formula 19:

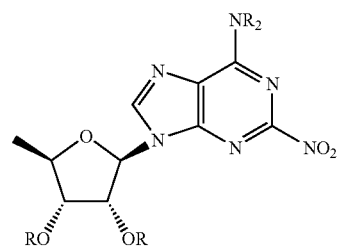

wherein each R is independently a protecting group.

A method of producing a compound of formula 20 as defined in Example 1, which comprises reacting a compound of general formula (D) with cyclopentylamine and de-protecting the reaction product to produce the compound of formula 20.

A method of producing a compound of formula 21 as defined in Example 1, which comprises reacting a compound of the following general formula (E) with cyclopentylamine and de-protecting the reaction product to produce the compound of formula 21:

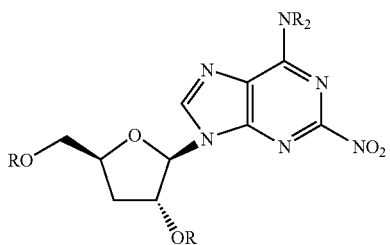

wherein each R is independently a protecting group.

Chemical structures of compounds of the invention are given in the Examples below. Binding experiments were carried out using rat A2a receptors. Ki values were determined for each compound at pH 5.5 and pH 7.4. To calculate this, rat striatal membranes were incubated for 90 minutes at 22° C. in the presence of 2 nM [3H]-CGS21680, 1 Unit/ml adenosine deaminase and increasing concentrations of the compound being studied, prior to filtration and liquid scintillation counting. The Ki values of the compounds were found to be in the range 0.96-220 nM at pH 5.5, and in the range 47-25000 nM at pH 7.4. $Ki_{pH\,7.4}/Ki_{pH\,5.5}$ for each compound is in the range 6-5400.

EXAMPLE 1

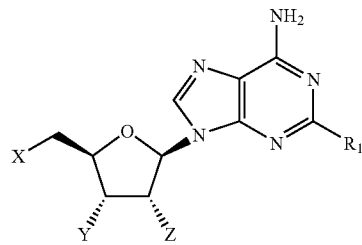

| Compound No. | Structure $R_1$ |
|---|---|
| When X = Y = Z = OH | |
| 1 | $OCH_2CF_2CF_3$ |
| 2 | $O-(3-((4-(CF_3))Ph))Ph$ |
| 3 | $O-(3,4-Cl_2)Ph$ |
| 4 | $O-(3-CF_3,4-F)Ph$ |
| 5 | $O-(3-CF_3,4-Cl)Ph$ |
| 6 | $O-(3-Cl,4-CN)Ph$ |
| 7 | $O-(3,5-(CF_3)_2)Ph$ |
| 8 | 1-Piperazinyl(4-((3,4-Cl$_2$)Ph)) |
| 9 | $(3,4-Cl_2)Ph$ |
| 10 | $(3,5-F_2)Ph$ |
| 11 | $(3,5-(CF_3)_2)Ph$ |
| 12 | $(3,4,5-F_3)Ph$ |
| 13 | (2-Benzofuranyl) |
| When X = Y = OH and Z = OMe | |
| 14 | $OCH_3$ |
| 15 | $OCH_2CHF_2$ |
| 16 | $OCH_2Cyclopentyl$ |
| 17 | $O-(2,5-F_2)Ph$ |
| 18 | $NH-(S)-CH(CH_3)CH_2CH_3$ |
| When X = H and Y = Z = OH | |
| 19 | $NHCH_2CH_2CH_2CH_2CH_2CH_3$ |
| 20 | NHCyclopentyl |
| When X = Z = OH and Y = H | |
| 21 | NHCyclopentyl |

EXAMPLE 2

Preparation of (2R,3R,4S,5R)-2-[6-amino-2-(2,2,3,3,3-pentafluoropropoxy)-9H-purin-9-yl]-5-(hydroxymethyl)tetrahydrofuran-3,4-diol 1

Scheme 1

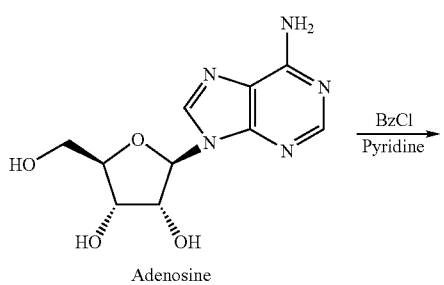

Adenosine

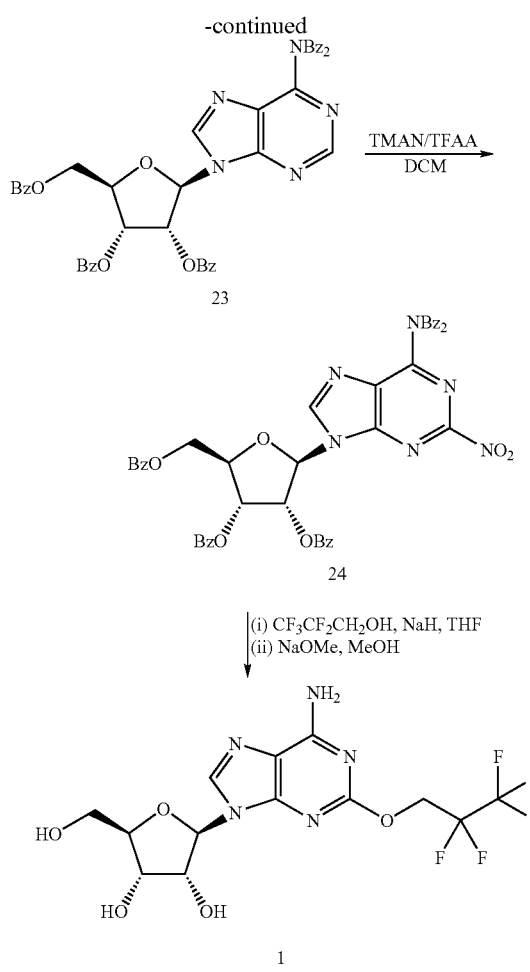

in vacuo and the residue purified by reverse phase column chromatography (LiChroprep RP-18, 40-63 μm, 230×26 mm (50 g), 30 mL per min, gradient 0-100% methanol in water over 45 min, product eluted in 60% methanol) and reverse phase prep HPLC (Phenomenex Synergi, RP-Hydro 150×10 mm, 10μ, 20 mL per min, gradient 5-100% acetonitrile in water over 25 min, product eluted in 36% acetonitrile) to yield (2R,3R,4S,5R)-2-[6-amino-2-(2,2,3,3,3-pentafluoropropoxy)-9H-purin-9-yl]-5-(hydroxymethyl)tetrahydrofuran-3,4-diol 1 as a white solid (26 mg, 13%).

HPLC (Phenomenex Synergi, RP-Hydro, 150×4.6 mm, 4u, 1.5 mL per min, 30° C., gradient 5-100% acetonitrile (+0.085% trifluoroacetic acid (TFA)) in water (+0.1% TFA) over 7 min—held for 30 s, 200-300 nm): Retention time 4.13 min, 99.01%.

LCMS (Phenomenex Synergi, RP-Hydro, 150×4.6 mm, 4u, 1.5 mL per min, 30° C., gradient 5-100% acetonitrile (+0.085% TFA) in water (+0.1% TFA) over 7 min—held for 30 s, 200-300 nm): Retention time 5.90 min, 100%, ES$^+$: 416.392 [MH]$^+$.

EXAMPLE 3

Preparation of (2R,3R,4S,5R)-2-(6-amino-2-{[4'-(trifluoromethyl)biphenyl-3-yl]oxy}-9H-purin-9-yl)-5-(hydroxymethyl)tetrahydrofuran-3,4-diol 2

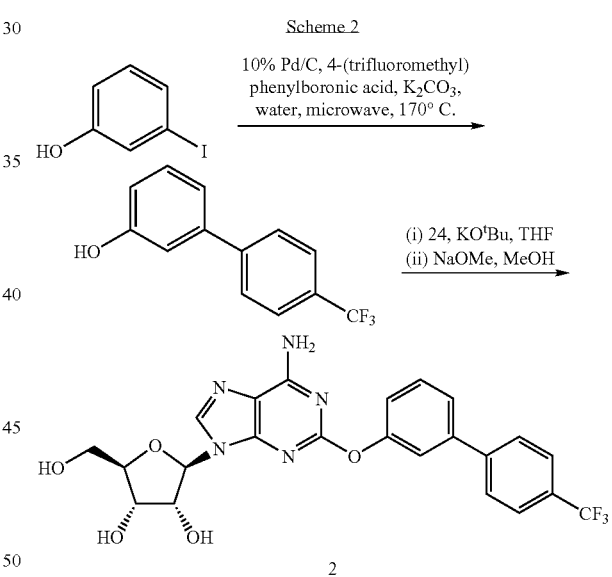

To a solution of adenosine (26.7 g, 0.1 mol) in pyridine (300 mL) was added benzoyl chloride (81.2 mL, 698 mmol) and the resulting solution was refluxed at 80° C. for 4 h. The solvents were removed in vacuo and the residue dissolved in EtOAc and washed with aq. NaHCO$_3$, brine and water, and the organic phase dried over MgSO$_4$. Crystallisation from dichloromethane (DCM)/ethanol afforded 23 as a white crystalline solid in 2 batches (54 g and 10 g, 82% overall).

To a solution of tetramethylammonium nitrate (TMAN) (2.61 g, 19.2 mmol) in DCM (37 mL) was added trifluoroacetic anhydride (TFAA) (2.67 mL, 19.2 mmol) and the resulting solution stirred for 1 h. The mixture was cooled to 0° C. and a solution of 23 (10.1 g, 12.7 mmol) in DCM (37 mL) was added. The resulting solution was allowed to warm to rt over 4 h. The solution was then washed with aq. NaHCO$_3$, brine and water (×3) and the organic phase dried over MgSO$_4$. Crystallisation from DCM/ethanol afforded 24 as a pale yellow solid (7.2 g, 68%).

To a solution of CF$_3$CF$_2$CH$_2$OH (58 μL, 0.58 mmol) in tetrahydrofuran (THF) (10 mL) was added NaH (23 mg, 60% dispersion in mineral oil, 0.58 mmol) and the resulting suspension stirred for 1 h. 24 (400 mg, 0.48 mmol) was then added and the resulting solution stirred for 4 d. A further 0.5 eq of CF$_3$CF$_2$CH$_2$ONa in THF (5 mL), prepared as above, was then added and stirring continued for 16 h. The solvents were then removed in vacuo and the residue dissolved in methanol before the addition of NaOMe (cat) and stirring of the resulting suspension for 16 h. The solvents were removed To a mixture of 10% Pd/C (cat), 3-iodophenol (220 mg, 1.00 mmol) and 4-(trifluoromethyl)phenylboronic acid (284 mg, 1.49 mmol) was added a solution of K$_2$CO$_3$ (415 mg, 3.01 mmol) in water (10 mL) and the reaction mixture was heated in a Biotage microwave (170° C., absorption high, pre-stirring 10 s) for 20 min. The crude reaction mixture was then extracted into EtOAc (40 mL×3) and dried over MgSO$_4$ to yield 3-(4-(trifluoromethyl)phenyl)phenol as a yellow solid (212 mg, 89%, 99% purity by HPLC) which was used without further purification.

To a solution of 3-(4-(trifluoromethyl)phenyl)phenol (212 mg, 0.89 mmol) in THF was added KO$^t$Bu (100 mg, 0.89 mmol) and the resulting suspension stirred for 30 min before being added to a solution of 24 (400 mg, 0.48 mmol) in THF. Stirring was continued for 4 d and the solvents were then removed in vacuo. The residue was dissolved in methanol (10 mL), NaOMe (cat) was added and the resulting mixture was stirred for 16 h. The solvents were removed in vacuo and the residue purified by flash column chromatography (normal phase, ICN silica, 18-32μ, gradient 5-15% ethanol in DCM, residue dry loaded) and reverse phase prep HPLC (Phenomenex Synergi, RP-Hydro 150×10 mm, 10%, 20 mL per min, gradient 5-100% acetonitrile in water over 10 min, product eluted in 55% acetonitrile) to yield (2R,3R,4S,5R)-2-(6-amino-2-{[4'-(trifluoromethyl)biphenyl-3-yl]oxy}-9H-purin-9-yl)-5-(hydroxymethyl)tetrahydrofuran-3,4-diol 2 as a white solid (51 mg, 21%).

HPLC (Phenomenex Synergi, RP-Hydro, 150×4.6 mm, 4 u, 1.5 mL per min, 30° C., gradient 5-100% acetonitrile (+0.085% TFA) in water (+0.1% TFA) over 7 min—held for 30 s, 200-300 nm): Retention time 5.37 min, 98.87%.

LCMS (Phenomenex Synergi, RP-Hydro, 150×4.6 mm, 4u, 1.5 mL per min, 30° C., gradient 5-100% acetonitrile (+0.085% TFA) in water (+0.1% TFA) over 7 min—held for 30 s, 200-300 nm): Retention time 5.76 min, 100%, ES$^+$: 504.412 [MH]$^+$.

EXAMPLE 4

Preparation of (2R,3R,4S,5R)-2-[6-amino-2-(3,4-dichlorophenoxy)-9H-purin-9-yl]-5-(hydroxymethyl)tetrahydrofuran-3,4-diol 3

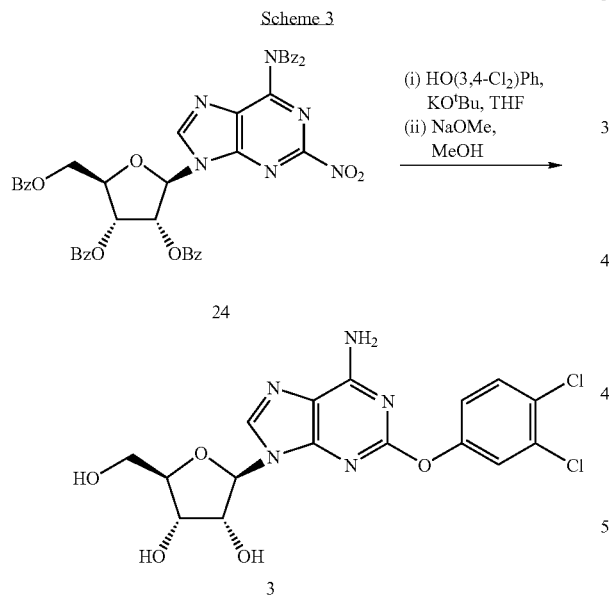

To a solution of 3,4-dichlorophenol (157 mg, 0.96 mmol) in THF (3 mL) was added KO$^t$Bu (108 mg, 0.96 mmol) and the resulting suspension stirred for 1.5 h before being added to a solution of 24 (400 mg, 0.48 mmol) in THF. Stirring was continued for 2 d and the solvents were then removed in vacuo. The residue was dissolved in methanol (15 mL), NaOMe (cat) was added and the resulting mixture was stirred for 4 d. The solvents were removed in vacuo and the residue purified by reverse phase column chromatography (LiChroprep RP-18, 40-63 μm, 230×26 mm (50 g), 30 mL per min, gradient 0-100% methanol in water over 45 min, product eluted in 72% methanol) and reverse phase prep HPLC (Phenomenex Synergi, RP-Hydro 150×10 mm, 10μ, 20 mL per min, gradient 5-100% acetonitrile in water over 10 min, product eluted in 45% acetonitrile) to yield (2R,3R,4S,5R)-2-[6-amino-2-(3,4-dichlorophenoxy)-9H-purin-9-yl]-5-(hydroxymethyl)tetrahydrofuran-3,4-diol 3 as a white solid (15 mg, 7.6%).

HPLC (Phenomenex Synergi, RP-Hydro, 150×4.6 mm, 4u, 1.5 mL per min, 30° C., gradient 5-100% acetonitrile (+0.085% TFA) in water (+0.1% TFA) over 7 min—held for 30 s, 200-300 nm): Retention time 4.42 min, 98.42%.

LCMS (Phenomenex Synergi, RP-Hydro, 150×4.6 mm, 4u, 1.5 mL per min, 30° C., gradient 5-100% acetonitrile (+0.085% TFA) in water (+0.1% TFA) over 7 min—held for 30 s, 200-300 nm): Retention time 5.31 min, 100%, ES$^+$: 428.3 [MH]$^+$.

EXAMPLE 5

Preparation of (2R,3R,4S,5R)-2-{6-amino-2-[4-fluoro-3-(trifluoromethyl)phenoxy]-9H-purin-9-yl}-5-(hydroxymethyl)tetrahydrofuran-3,4-diol 4

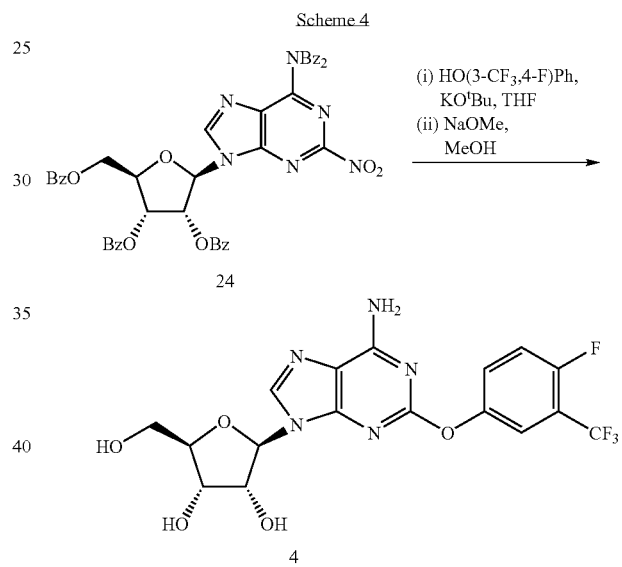

To a solution of 3-trifluoromethyl,4-fluorophenol (173 mg, 0.96 mmol) in THF (3 mL) was added KO$^t$Bu (108 mg, 0.96 mmol) and the resulting suspension stirred for 1.5 h before being added to a solution of 24 (400 mg, 0.48 mmol) in THF (15 mL). Stirring was continued for 20 h and the solvents were then removed in vacuo. The residue was dissolved in methanol (15 mL), NaOMe (cat) was added and the resulting mixture was stirred for 4 d. The solvents were removed in vacuo and the residue purified by reverse phase column chromatography (LiChroprep RP-18, 40-63 μm, 230×26 mm (50 g), 30 mL per min, gradient 0-100% methanol in water over 45 min, product eluted in 70% methanol), reverse phase prep HPLC (Phenomenex Synergi, RP-Hydro 150×10 mm, 10μ, 20 mL per min, gradient 5-100% acetonitrile in water over 10 min, product eluted in 50% acetonitrile) and recrystallisation from ethanol/heptane to yield (2R,3R,4S,5R)-2-{6-amino-2-[4-fluoro-3-(trifluoromethyl)phenoxy]-9H-purin-9-yl}-5-(hydroxymethyl)tetrahydrofuran-3,4-diol 44 as a white solid (23 mg, 11%).

HPLC (Phenomenex Synergi, RP-Hydro, 150×4.6 mm, 4 u, 1.5 mL per min, 30° C., gradient 5-100% acetonitrile (+0.085% TFA) in water (+0.1% TFA) over 7 min—held for 30 s, 200-300 nm): Retention time 4.43 min, 98.00%.

LCMS (Phenomenex Synergi, RP-Hydro, 150×4.6 mm, 4u, 1.5 mL per min, 30° C., gradient 5-100% acetonitrile (+0.085% TFA) in water (+0.1% TFA) over 7 min—held for 30 s, 200-300 nm): Retention time 5.29 min, 100%, ES+: 446.295 [MH]+.

EXAMPLE 6

Preparation of (2R,3R,4S,5R)-2-{6-amino-2-[4-chloro-3-(trifluoromethyl)phenoxy]-9H-purin-9-yl}-5-(hydroxymethyl)tetrahydrofuran-3,4-diol 5

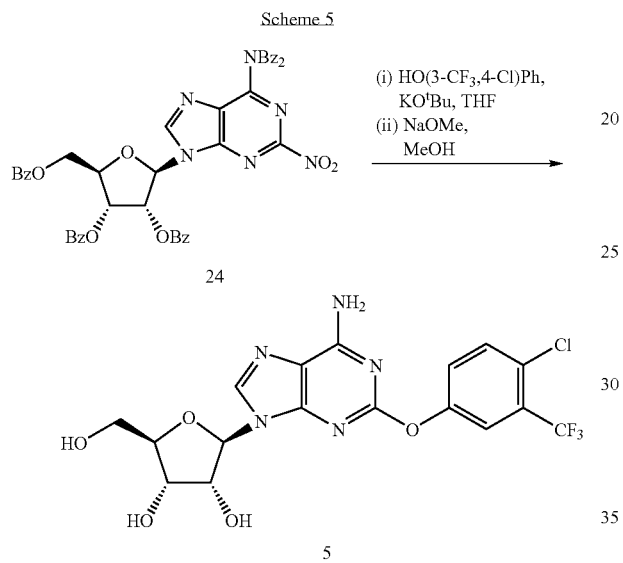

To a solution of 3-trifluoromethyl,4-chlorophenol (582 mg, 2.96 mmol) in THF (10 mL) was added KO$^t$Bu (332 mg, 2.96 mmol) and the resulting suspension stirred for 2 h before being added to a solution of 24 (1.66 g, 2.00 mmol) in THF (100 mL). Stirring was continued for 2 d and the solvents were then removed in vacuo. The residue was dissolved in methanol (40 mL), NaOMe (170 mg, 3.15 mmol) was added and the resulting mixture was stirred for 16 h. The solvents were removed in vacuo and the residue purified by flash column chromatography (normal phase, ICN silica, 18-32μ, gradient 5-20% ethanol in DCM, residue dry loaded) and twice by reverse phase column chromatography (LiChroprep RP-18, 40-63 μm, 460×26 mm (100 g), 30 mL per min, gradient 0-100% methanol in water over 45 min, product eluted in 86% methanol) and (LiChroprep RP-18, 40-63 μm, 230×26 mm (50 g), 30 mL per min, gradient 0-100% methanol in water over 45 min, product eluted in 69% methanol) to yield (2R,3R,4S,5R)-2-{6-amino-2-[4-chloro-3-(trifluoromethyl)phenoxy]-9H-purin-9-yl}-5-(hydroxymethyl)tetrahydrofuran-3,4-diol 5 as a pale orange solid (188 mg, 20%).

HPLC (Phenomenex Synergi, RP-Hydro, 150×4.6 mm, 4u, 1.5 mL per min, 30° C., gradient 5-100% acetonitrile (+0.085% TFA) in water (+0.1% TFA) over 7 min—held for 30 s, 200-300 nm): Retention time 4.92 min, 99.68%.

LCMS (Phenomenex Synergi, RP-Hydro, 150×4.6 mm, 4u, 1.5 mL per min, 30° C., gradient 5-100% acetonitrile (+0.085% TFA) in water (+0.1% TFA) over 7 min—held for 30 s, 200-300 nm): Retention time 5.30 min, 100% ES+: 461.859 [MH]+.

EXAMPLE 7

Preparation of (2R,3R,4S,5R)-2-(6-amino-2-(3-chloro,4-cyanophenoxy)-9H-purin-9-yl)-5-(hydroxymethyl)tetrahydrofuran-3,4-diol 6

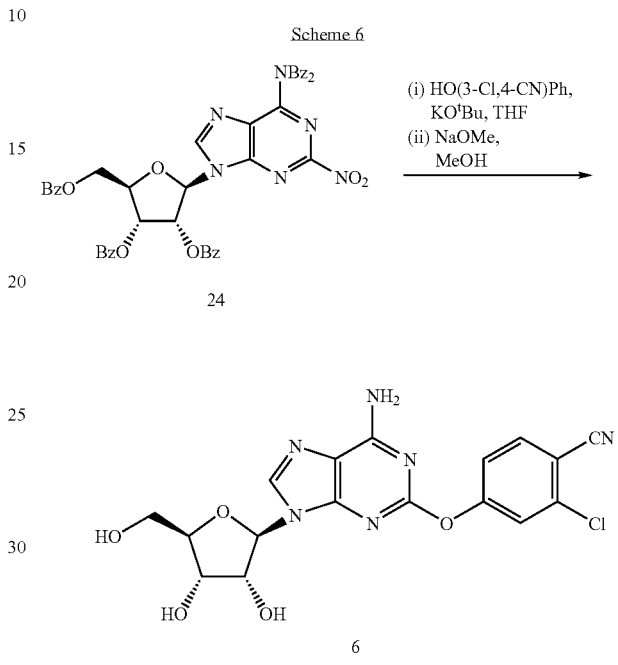

To a solution of 3-chloro,4-cyanophenol (147 mg, 0.96 mmol) in THF (5 mL) was added KO$^t$Bu (108 mg, 0.96 mmol) and the resulting suspension stirred for 30 min before being added to a solution of 24 (400 mg, 0.48 mmol) in THF (20 mL). Stirring was continued for 2 d and the solvents were then removed in vacuo. The residue was dissolved in methanol (20 mL), NaOMe (cat) was added and the resulting mixture was stirred for 16 h. The solvents were removed in vacuo and the residue purified by flash column chromatography (normal phase, ICN silica, 18-32%, gradient 5-20% ethanol in DCM, residue dry loaded) and by reverse phase prep HPLC (Phenomenex Synergi, RP-Hydro 150×10 mm, 10%, 20 mL per min, gradient 5-100% acetonitrile in water over 10 min, product eluted in 40% acetonitrile) to yield (2R,3R,4S,5R)-2-(6-amino-2-(3-chloro,4-cyanophenoxy)-9H-purin-9-yl)-5-(hydroxymethyl)tetrahydrofuran-3,4-diol 6 as a white solid (11 mg, 5.5%).

HPLC (Phenomenex Synergi, RP-Hydro, 150×4.6 mm, 4u, 1.5 mL per min, 30° C., gradient 5-100% acetonitrile (+0.085% TFA) in water (+0.1% TFA) over 7 min—held for 30 s, 200-300 nm): Retention time 4.01 min, 99.17%.

LCMS (Phenomenex Synergi, RP-Hydro, 150×4.6 mm, 4u, 1.5 mL per min, 30° C., gradient 5-100% acetonitrile (+0.085% TFA) in water (+0.1% TFA) over 7 min—held for 30 s, 200-300 nm n): Retention time 5.69 min, 100%, ES+: 419.35 [MH]+.

EXAMPLE 8

Preparation of (2R,3R,4S,5R)-2-(6-amino-2-[3,5-bis(trifluoromethyl)phenoxy]-9H-purin-9-yl)-5-(hydroxymethyl)tetrahydrofuran-3,4-diol 7

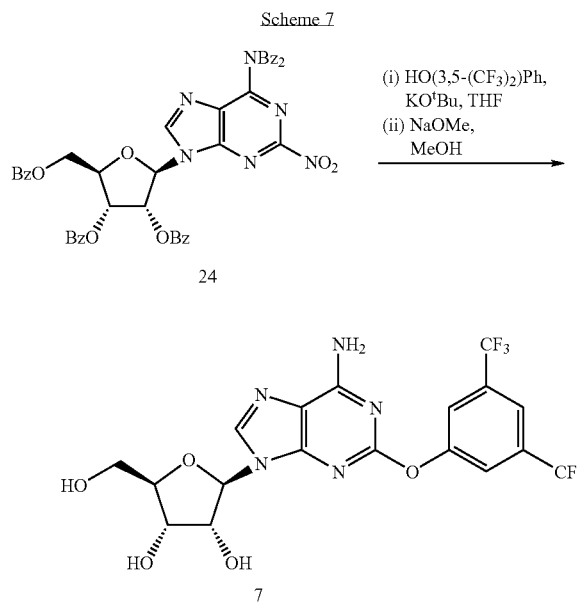

To a solution of 3,5-bis(trifluoromethyl)phenol (0.146 mL, 0.96 mmol) in THF (5 mL) was added KO$^t$Bu (108 mg, 0.96 mmol) and the resulting suspension stirred for 45 min before being added to a solution of 24 (400 mg, 0.48 mmol) in THF (20 mL). Stirring was continued for 47 h and the solvents were then removed in vacuo. The residue was dissolved in methanol (15 mL), NaOMe (cat) was added and the resulting mixture was stirred for 3 d. The solvents were removed in vacuo and the residue purified by reverse phase column chromatography (LiChroprep RP-18, 40-63 μm, 230×26 mm (50 g), 30 mL per min, gradient 0-100% methanol in water over 45 min, product eluted in 80% methanol) and reverse phase prep HPLC (Phenomenex Synergi, RP-Hydro 150×10 mm, 10μ, 20 mL per min, gradient 5-100% acetonitrile in water over 25 min, product eluted in 55% acetonitrile) to yield (2R,3R,4S,5R)-2-(6-amino-2-[3,5-bis(trifluoromethyl)phenoxy]-9H-purin-9-yl)-5-(hydroxymethyl)tetrahydrofuran-3,4-diol 7 as a white solid (28 mg, 12%).

HPLC (Phenomenex Synergi, RP-Hydro, 150×4.6 mm, 4u, 1.5 mL per min, 30° C., gradient 5-100% acetonitrile (+0.085% TFA) in water (+0.1% TFA) over 7 min—held for 30 s, 200-300 nm): Retention time 4.99 min, 98.54%.

LCMS (Phenomenex Synergi, RP-Hydro, 150×4.6 mm, 4u, 1.5 mL per min, 30° C., gradient 5-100% acetonitrile (+0.085% TFA) in water (+0.1% TFA) over 7 min—held for 30 s, 200-300 nm): Retention time 6.28 min, 100%, ES$^+$: 496.342 [MH]$^+$.

EXAMPLE 9

Preparation of (2R,3R,4S,5R)-2-(6-amino-2-(4-(3,4-dichlorophenyl)piperazin-1-yl)-9H-purin-9-yl)-5-(hydroxymethyl)tetrahydrofuran-3,4-diol 8

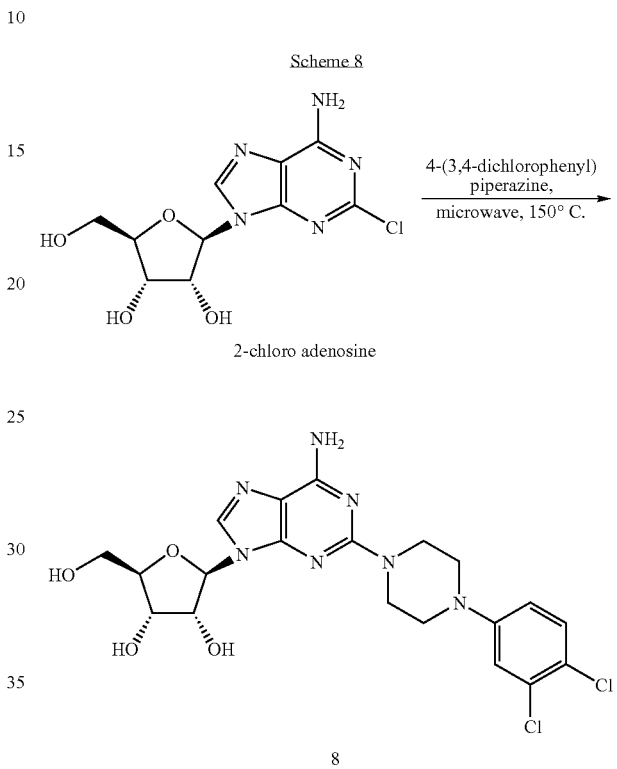

To a solution of 2-chloro adenosine (80 mg, 0.27 mmol) in THF (4 mL) was added 4-(3,4-dichlorophenyl)piperazine (122 mg, 0.53 mmol) and the resulting solution heated in a Biotage microwave (150° C., absorption high, pre-stirring 30 s) for 30 min. The solvents were then removed in vacuo and the residue purified twice by reverse phase prep HPLC (Phenomenex Synergi, RP-Hydro 150×10 mm, 10μ, 20 mL per min, gradient 5-100% acetonitrile in water over 18 min, product eluted in 80% acetonitrile) and (Phenomenex Synergi, RP-Hydro 150×10 mm, 10μ, 20 mL per min, gradient 5-100% acetonitrile in water over 9 min, product eluted in 55% acetonitrile) to yield (2R,3R,4S,5R)-2-(6-amino-2-(4-(3,4-dichlorophenyl)piperazin-1-yl)-9H-purin-9-yl)-5-(hydroxymethyl)tetrahydrofuran-3,4-diol 8 as a white solid (7.9 mg, 6%)

HPLC (Phenomenex Synergi, RP-Hydro, 150×4.6 mm, 4u, 1.5 mL per min, 30° C., gradient 5-100% acetonitrile (+0.085% TFA) in water (+0.1% TFA) over 7 min—held for 30 s, 200-300 nm): Retention time 4.78 min, 99.26%.

LCMS (Phenomenex Synergi, RP-Hydro, 150×4.6 mm, 4u, 1.5 mL per min, 30° C., gradient 5-100% acetonitrile (+0.085% TFA) in water (+0.1% TFA) over 7 min—held for 30 s, 200-300 nm): Retention time 5.82 min, 100%, ES$^+$: 496.3 [MH]$^+$.

EXAMPLE 10

Preparation of (2R,3R,4S,5R)-2-{6-amino-2-(3,4-dichlorophenyl)-9H-purin-9-yl}-5-(hydroxymethyl)tetrahydrofuran-3,4-diol 9

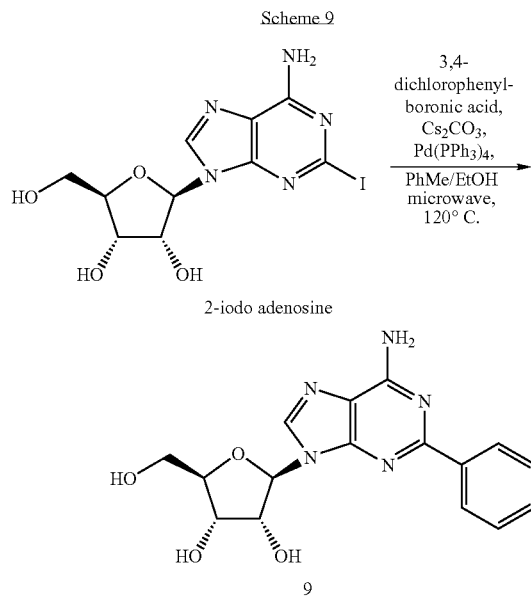

Scheme 9

A solution of 2-iodo adenosine (200 mg, 0.51 mmol), 3,4-dichlorophenylboronic acid (116 mg, 0.61 mmol), cesium carbonate (364 mg, 1.12 mmol) and Pd(PPh$_3$)$_4$ (59 mg, 0.051 mmol) in toluene (1.2 mL) and ethanol (2.4 mL) was heated in a Biotage microwave (120° C., absorption high, pre-stirring 30 s) for 110 min. The solvents were then removed in vacuo and the residue dissolved in EtOAc (30 mL) and washed with sat. aq. NaHCO$_3$ (20 mL×2) and brine (20 mL) and dried over MgSO$_4$. Purification by flash column chromatography (normal phase, ICN silica, 20 g, 18-32%, gradient 2.5-20% ethanol in DCM, residue dry loaded) and twice by reverse phase prep HPLC (Phenomenex Synergi, RP-Hydro 150×10 mm, 10µ, 20 mL per min, gradient 5-100% acetonitrile in water over 10 min, product eluted in 48% acetonitrile) and (Phenomenex Synergi, RP-Hydro 150×10 mm, 10µ, 20 mL per min, gradient 5-100% acetonitrile in water over 10 min, product eluted in 50% acetonitrile) afforded (2R,3R,4S,5R)-2-{6-amino-2-(3,4-dichlorophenyl)-9H-purin-9-yl}-5-(hydroxymethyl)tetrahydrofuran-3,4-diol 9 as a white solid (24.4 mg, 11%).

HPLC (Phenomenex Synergi, RP-Hydro, 150×4.6 mm, 4u, 1.5 mL per min, 30° C., gradient 5-100% acetonitrile (+0.085% TFA) in water (+0.1% TFA) over 7 min—held for 30 s, 200-300 nm): Retention time 4.77 min, 100%.

LCMS (Phenomenex Synergi, RP-Hydro, 150×4.6 mm, 4u, 1.5 mL per min, 30° C., gradient 5-100% acetonitrile (+0.085% TFA) in water (+0.1% TFA) over 7 min—held for 30 s, 200-300 nm): Retention time 5.19 min, 100%, ES$^+$: 412.32 [MH]$^+$.

EXAMPLE 11

Preparation of (2R,3R,4S,5R)-2-[6-amino-2-(3,5-difluorophenyl)-9H-purin-9-yl]-5-(hydroxymethyl)tetrahydrofuran-3,4-diol 10

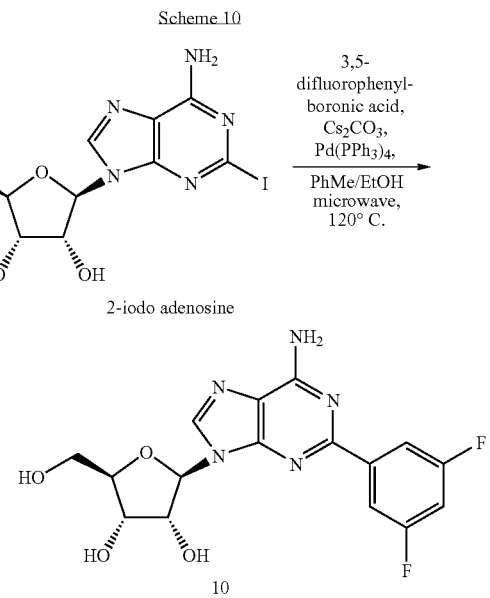

Scheme 10

A solution of 2-iodo adenosine (200 mg, 0.51 mmol), 3,5-difluorophenylboronic acid (150 mg, 0.95 mmol), cesium carbonate (364 mg, 1.12 mmol) and Pd(PPh$_3$)$_4$ (59 mg, 0.051 mmol) in toluene (1.2 mL) and ethanol (2.4 mL) was heated in a Biotage microwave (120° C., absorption high, pre-stirring 15 s) for 40 min. The solvents were then removed in vacuo and the residue dissolved in EtOAc (20 mL) and washed with sat. aq. NaHCO$_3$ (20 mL×2) and brine (20 mL) and dried over MgSO$_4$. Purification by reverse phase prep HPLC in 2 batches (Phenomenex Synergi, RP-Hydro 150×10 mm, 10%, 20 mL per min, gradient 5-100% acetonitrile in water over 10 min, product eluted in 35% acetonitrile) and (Phenomenex Synergi, RP-Hydro 150×10 mm, 10µ, 20 mL per min, gradient 5-100% acetonitrile in water over 10 min, product eluted in 40% acetonitrile), combination of the purer fractions from both columns, concentration in vacuo to ~20 mL and filtration of the resulting white precipitate gave (2R,3R,4S,5R)-2-{6-amino-2-(3,5-difluorophenyl)-9H-purin-9-yl}-5-(hydroxymethyl)tetrahydrofuran-3,4-diol 10 as a white solid (16.8 mg, 9%).

HPLC (Phenomenex Synergi, RP-Hydro, 150×4.6 mm, 4u, 1.5 mL per min, 30° C., gradient 5-100% acetonitrile (+0.085% TFA) in water (+0.1% TFA) over 7 min—held for 30 s, 200-300 nm): Retention time 4.07 min, 99.86%.

LCMS (Phenomenex Synergi, RP-Hydro, 150×4.6 mm, 4u, 1.5 mL per min, 30° C., gradient 5-100% acetonitrile (+0.085% TFA) in water (+0.1% TFA) over 7 min—held for 30 s, 200-300 nm): Retention time 6.02 min, 100%, ES$^+$: 380.4 [MH]$^+$.

EXAMPLE 12

Preparation of (2R,3R,4S,5R)-2-{6-amino-2-[3,5-bis(trifluoromethyl)phenyl]-9H-purin-9-yl}-5-(hydroxymethyl)tetrahydrofuran-3,4-diol 11

EXAMPLE 13

Preparation of (2R,3R,4S,5R)-2-{6-amino-2-(3,4,5-trifluorophenyl)-9H-purin-9-yl}-5-(hydroxymethyl)tetrahydrofuran-3,4-diol 12

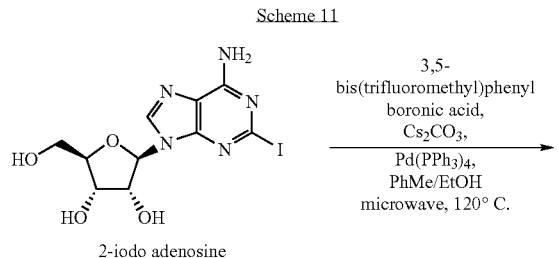

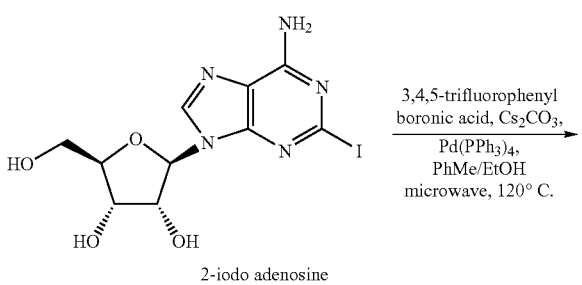

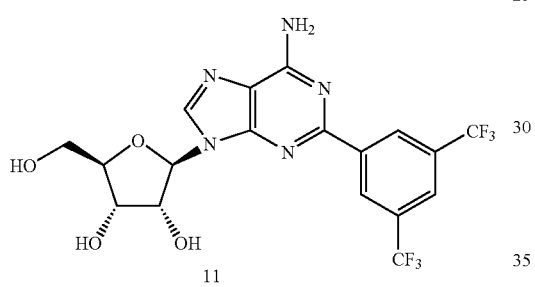

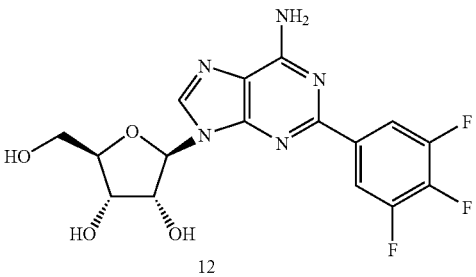

A solution of 2-iodo adenosine (1.00 g, 2.53 mmol), 3,5-bis(trifluoromethyl)phenylboronic acid (784 mg, 3.04 mmol), cesium carbonate (1.81 g, 6.08 mmol) and Pd(PPh$_3$)$_4$ (293 mg, 0.25 mmol) in toluene (2.4 mL) and ethanol (4.8 mL) was heated in a Biotage microwave (120° C., absorption high, pre-stirring 30 s) for 40 min in 2 batches and the crude reaction mixtures were combined. The solvents were then removed in vacuo and the residue dissolved in EtOAc (200 mL) and washed with sat. aq. NaHCO$_3$ (100 mL) and brine (100 mL). Purification by flash column chromatography (normal phase, ICN silica, 50 g, 18-32µ, gradient 5-25% ethanol in DCM, residue dry loaded, product eluted in 25% ethanol) afforded (2R,3R,4S,5R)-2-{6-amino-2-[3,5-bis(trifluoromethyl)phenyl]-9H-purin-9-yl}-5-(hydroxymethyl)tetrahydrofuran-3,4-diol 11 as an off-white glass (364 mg, 30%).

HPLC (Phenomenex Synergi, RP-Hydro, 150×4.6 mm, 4u, 1.5 mL per min, 30° C., gradient 5-100% acetonitrile (+0.085% TFA) in water (+0.1% TFA) over 7 min—held for 30 s, 200-300 nm): Retention time 5.46 min, 99.86%.

LCMS (Phenomenex Synergi, RP-Hydro, 150×4.6 mm, 4u, 1.5 mL per min, 30° C., gradient 5-100% acetonitrile (+0.085% TFA) in water (+0.1% TFA) over 7 min—held for 30 s, 200-300 nm): Retention time 5.89 min, 100%, ES$^+$: 479.886 [MH]$^+$.

A solution of 2-iodo adenosine (200 mg, 0.51 mmol), 3,4,5-trifluorophenylboronic acid (107 mg, 0.609 mmol), cesium carbonate (364 mg, 1.12 mmol) and Pd(PPh$_3$)$_4$ (59 mg, 0.051 mmol) in toluene (1.2 mL) and ethanol (2.4 mL) was heated in a Biotage microwave (120° C., absorption high, pre-stirring 30 s) for 40 min. The solvents were then removed in vacuo and the residue dissolved in EtOAc (30 mL) and washed with sat. aq. NaHCO$_3$ (20 mL×2) and brine (20 mL) and dried over MgSO$_4$. Purification by flash column chromatography (normal phase, ICN silica, 50 g, 18-32%, gradient 2.5-15% ethanol in DCM, residue dry loaded, product eluted in 15% ethanol) and by reverse phase prep HPLC (Phenomenex Synergi, RP-Hydro 150×10 mm, 10µ, 20 mL per min, gradient 5-100% acetonitrile in water over 10 min, product eluted in 50% acetonitrile) afforded (2R,3R,4S,5R)-2-{6-amino-2-(3,4,5-trifluorophenyl)-9H-purin-9-yl}-5-(hydroxymethyl) tetrahydrofuran-3,4-diol 12 as a white solid (13.2 mg, 7%).

HPLC (Phenomenex Synergi, RP-Hydro, 150×4.6 mm, 4u, 1.5 mL per min, 30° C., gradient 5-100% acetonitrile (+0.085% TFA) in water (+0.1% TFA) over 7 min—held for 30 s, 200-300 nm): Retention time 4.49 min, 100%.

LCMS (Phenomenex Synergi, RP-Hydro, 150×4.6 mm, 4u, 1.5 mL per min, 30° C., gradient 5-100% acetonitrile (+0.085% TFA) in water (+0.1% TFA) over 7 min—held for 30 s, 200-300 nm): Retention time 5.04 min, 100%, ES$^+$: 398.396 [MH]$^+$.

EXAMPLE 14

Preparation of (2R,3R,4S,5R)-2-{6-amino-2-(benzofuran-2-yl)-9H-purin-9-yl}-5-(hydroxymethyl)tetrahydrofuran-3,4-diol 13

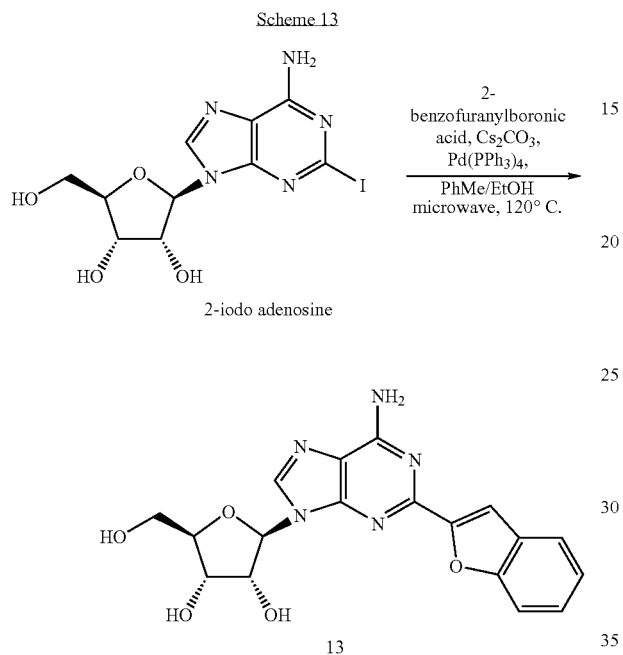

A solution of 2-iodo adenosine (200 mg, 0.51 mmol), 2-benzofuranylboronic acid (99 mg, 0.61 mmol), cesium carbonate (364 mg, 1.12 mmol) and Pd(PPh$_3$)$_4$ (59 mg, 0.051 mmol) in toluene (1.2 mL) and ethanol (2.4 mL) was heated in a Biotage microwave (120° C., absorption high, pre-stirring 15 s) for 40 min. The solvents were then removed in vacuo and the residue dissolved in EtOAc (15 mL) and washed with sat. aq. NaHCO$_3$ (15 mL×2) and brine (15 mL) and dried over MgSO$_4$. Purification by flash column chromatography (normal phase, ICN silica, 20 g, 18-32μ, gradient 0-20% ethanol in DCM, residue dry loaded, product eluted in 15% ethanol) and by reverse phase prep HPLC (Phenomenex Synergi, RP-Hydro 150×10 mm, 10%, 20 mL per min, gradient 5-100% acetonitrile in water over 10 min, product eluted in 35% acetonitrile) afforded the title compound 13 as a white solid (4.9 mg, 3%).

HPLC (Phenomenex Synergi, RP-Hydro, 150×4.6 mm, 4u, 1.5 mL per min, 30° C., gradient 5-100% acetonitrile (+0.085% TFA) in water (+0.1% TFA) over 7 min—held for 30 s, 200-300 nm): Retention time 4.13 min, 100%.

LCMS (Phenomenex Synergi, RP-Hydro, 150×4.6 mm, 4u, 1.5 mL per min, 30° C., gradient 5-100% acetonitrile (+0.085% TFA) in water (+0.1% TFA) over 7 min—held for 30 s, 200-300 nm): Retention time 4.61 min, 100%, ES$^+$: 384.469 [MH]$^+$.

EXAMPLE 15

Preparation of (2R,3R,4R,5R)-5-(6-amino-2-methoxy-9H-purin-9-yl)-2-(hydroxymethyl)-4-methoxytetrahydrofuran-3-ol 14

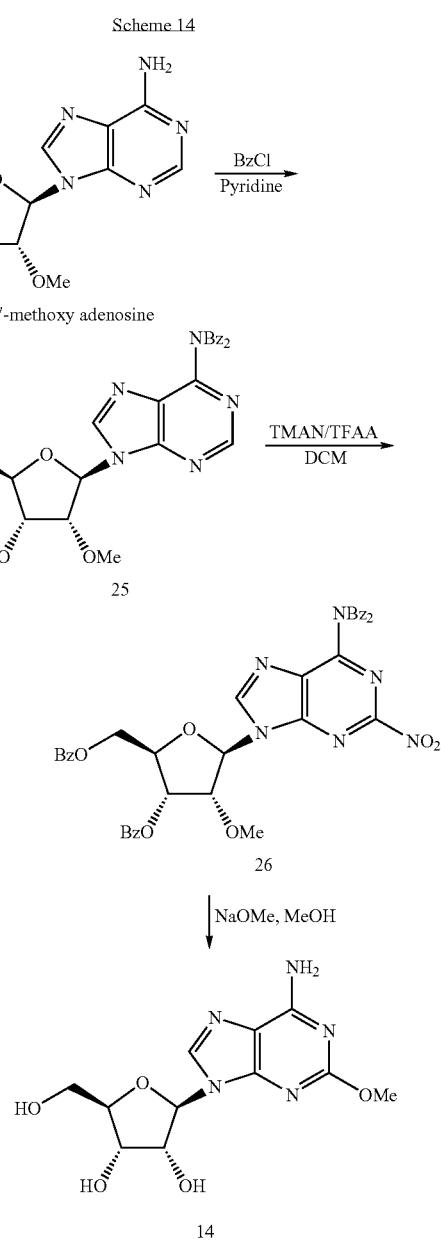

To a solution of 2'-methoxy adenosine (10 g, 35.6 mmol) in pyridine (75 mL) was added benzoyl chloride (22.7 mL, 196 mmol) and the resulting solution was refluxed at 80° C. for 4 h. The solvents were removed in vacuo and the residue dissolved in EtOAc and washed with aq. NaHCO$_3$, brine and water, and the organic phase dried over MgSO$_4$. Crystallisation from ethanol afforded 25 as a white solid in 2 batches (13.7 g and 4.3 g, 72% overall).

To a suspension of 25 (13.7 g, 19.7 mmol) and TMAN (3.48 g, 25.6 mmol) in DCM (100 mL) was added drop-wise a solution of TFAA (3.77 mL, 26.7 mmol) in DCM (20 mL)

and the resulting solution stirred for 2 h. The solution was then washed with aq. NaHCO$_3$ and water (×3) and the organic phase dried over MgSO$_4$. The residue was dissolved in ethanol (20 mL), DCM (50 mL) was added and the solvents were removed in vacuo to yield 26 as a pale yellow foam (14 g, 96%, 70% purity) which was used without further purification. To a solution of 26 (3.7 g, 5.31 mmol) in methanol (70 mL) was added NaOMe (1.15 g, 21.3 mmol) and the resulting solution stirred at room temperature for 2 d. Silica gel (15 g) was then added and the solvents removed in vacuo. Purification by flash column chromatography (normal phase, ICN silica, 18-32μ, gradient 10% ethanol in DCM, residue dry loaded) and recrystallisation from hot water afforded (2R,3R,4R,5R)-5-(6-amino-2-methoxy-9H-purin-9-yl)-2-(hydroxymethyl)-4-methoxytetrahydrofuran-3-ol 14 as a white crystalline solid (536 mg, 32%).

HPLC (Phenomenex Synergi, RP-Hydro, 150×4.6 mm, 4u, 1.5 mL per min, 30° C., gradient 5-100% acetonitrile (+0.085% TFA) in water (+0.1% TFA) over 7 min—held for 30 s, 200-300 nm): Retention time 2.80-2.86 min (split peak), 100%.

LCMS (Phenomenex Synergi, RP-Hydro, 150×4.6 mm, 4u, 1.5 mL per min, 30° C., gradient 5-100% acetonitrile (+0.085% TFA) in water (+0.1% TFA) over 7 min—held for 30 s, 200-300 nm): Retention time 3.42 min, 100%, ES$^+$: 312.063 [MH]$^+$.

EXAMPLE 16

Preparation of (2R,3R,4R,5R)-5-[6-amino-2-(2,2-difluoroethoxy)-9H-purin-9-yl]-2-(hydroxymethyl)-4-methoxytetrahydrofuran-3-ol 15

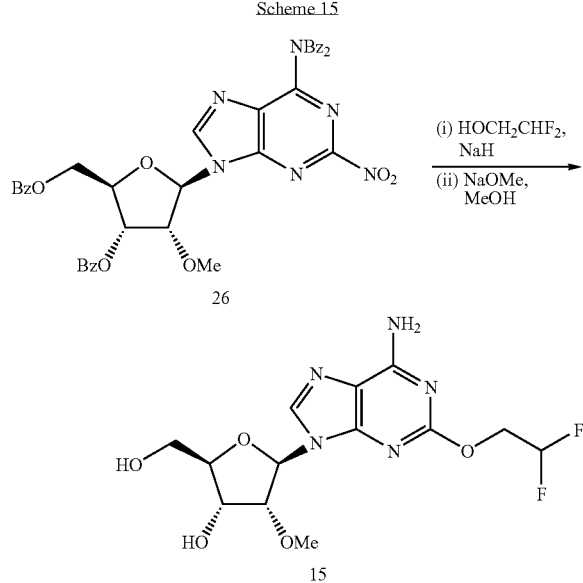

To a solution of CHF$_2$CH$_2$OH (0.165 mL, 2.60 mmol) in THF (10 mL) was added NaH (104 mg, 60% dispersion in mineral oil, 2.60 mmol) and the resulting suspension stirred for 1 h. A solution of 26 (956 mg, 1.37 mmol) in THF (10 mL) was then added and the resulting solution stirred at room temperature for 2 d. The solvents were then removed in vacuo and the residue dissolved in methanol (20 mL) before the addition of NaOMe (cat) and stirring of the resulting suspension for 16 h. The solvents were removed in vacuo and the residue purified by flash column chromatography (normal phase, ICN silica, 50 g, 18-32μ, gradient 2.5-15% ethanol in DCM, residue dry loaded, product eluted in 10-15% ethanol) and by reverse phase prep HPLC (Phenomenex Synergi, RP-Hydro 150×10 mm, 10μ, 20 mL per min, gradient 5-100% acetonitrile in water over 10 min, product eluted in 25% acetonitrile) to yield (2R,3R,4R,5R)-5-[6-amino-2-(2,2-difluoroethoxy)-9H-purin-9-yl]-2-(hydroxylmethyl)-4-methoxytetrahydrofuran-3-ol 15 as a white solid (134 mg, 27%).

HPLC (Phenomenex Synergi, RP-Hydro, 150×4.6 mm, 4u, 1.5 mL per min, 30° C., gradient 5-100% acetonitrile (+0.085% TFA) in water (+0.1% TFA) over 7 min—held for 30 s, 200-300 nm): Retention time 3.42 min, 100%.

LCMS (Phenomenex Synergi, RP-Hydro, 150×4.6 mm, 4u, 1.5 mL per min, 30° C., gradient 5-100% acetonitrile (+0.085% TFA) in water (+0.1% TFA) over 7 min—held for 30 s, 200-300 nm): Retention time 3.96 min, 100%, ES$^+$: 362.342 [MH]$^+$.

EXAMPLE 17

Preparation of (2R,3R,4R,5R)-5-[6-amino-2-(cyclopentylmethoxy)-9H-purin-9-yl]-2-(hydroxymethyl)-4-methoxytetrahydrofuran-3-ol 16

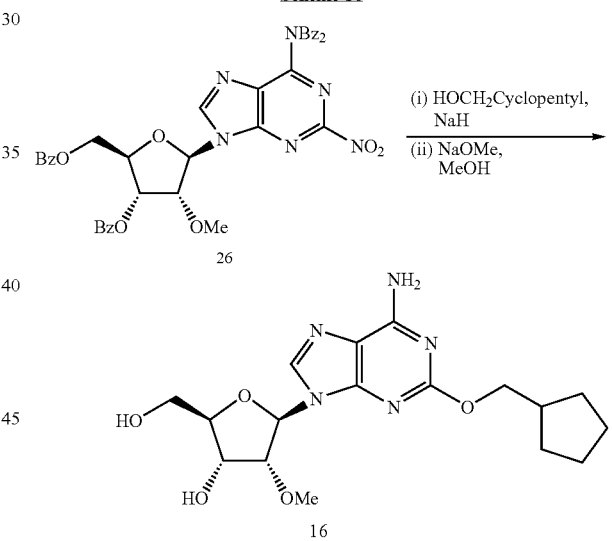

To a solution of cyclopentanemethanol (1.73 mL, 19.1 mmol) in THF (35 mL) was added NaH (637 mg, 60% dispersion in mineral oil, 15.9 mmol) and the resulting suspension stirred for 1 h. A solution of 26 (3.7 g, 5.31 mmol) in THF (35 mL) was then added and the resulting solution stirred at room temperature for 2 d. The solvents were then removed in vacuo and the residue dissolved in methanol (70 mL) before the addition of NaOMe (860 mg, 15.9 mmol) and stirring of the resulting suspension for 16 h. Silica gel (15 g) was then added and the solvents removed in vacuo. Purification by flash column chromatography (normal phase, ICN silica, 18-32μ, gradient 5-10% ethanol in DCM, residue dry loaded) and recrystallisation from methanol/water afforded (2R,3R,4R,5R)-5-[6-amino-2-(cyclopentylmethoxy)-9H-purin-9-yl]-2-(hydroxymethyl)-4-methoxytetrahydrofuran-3-ol 16 as a white crystalline solid (356 mg, 18%).

HPLC (Phenomenex Synergi, RP-Hydro, 150×4.6 mm, 4u, 1.5 mL per min, 30° C., gradient 5-100% acetonitrile (+0.085% TFA) in water (+0.1% TFA) over 7 min—held for 30 s, 200-300 nm): Retention time 4.27 min, 99.05%.

LCMS (Phenomenex Synergi, RP-Hydro, 150×4.6 mm, 4u, 1.5 mL per min, 30° C., gradient 5-100% acetonitrile (+0.085% TFA) in water (+0.1% TFA) over 7 min—held for 30 s, 200-300 nm): Retention time 4.76 min, 100%, ES+: 380.499 [MH]+.

EXAMPLE 18

Preparation of (2R,3R,4R,5R)-5-[6-amino-2-(2,5-difluorophenoxy)-9H-purin-9-yl]-2-(hydroxymethyl)-4-methoxytetrahydrofuran-3-ol 17

Scheme 17

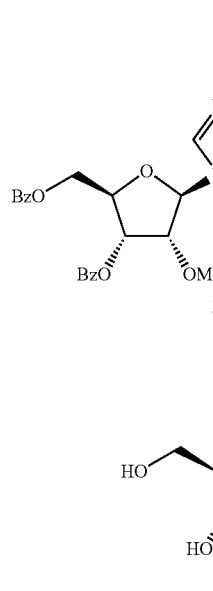

To a solution of 2,5-difluorophenol (104 mg, 0.80 mmol) in THF (7 mL) was added KO$^t$Bu (63 mg, 0.56 mmol) and the resulting suspension stirred for 30 min before the addition of 26 (295 mg, 0.42 mmol). Stirring was continued for 6 h and the solvents were then removed in vacuo. The residue was dissolved in methanol (7 mL), NaOMe (86 mg, 1.59 mmol) was added and the resulting mixture was stirred for 16 h, before being quenched with aq. citric acid. The solvents were removed in vacuo and the residue purified by reverse phase column chromatography (LiChroprep RP-18, 40-63 μm, 230×26 mm (50 g), 30 mL per min, gradient 5-100% methanol in water over 45 min, product eluted in 57% methanol) and reverse phase prep HPLC (Phenomenex Synergi, RP-Hydro 150×10 mm, 10μ, 20 mL per min, gradient 5-100% acetonitrile in water over 10 min, product eluted in 26% acetonitrile) to yield (2R,3R,4R,5R)-5-[6-amino-2-(2,5-difluorophenoxy)-9H-purin-9-yl]-2-(hydroxymethyl)-4-methoxytetrahydrofuran-3-ol 17 as a pale yellow solid (30.9 mg, 18%).

HPLC (Phenomenex Synergi, RP-Hydro, 150×4.6 mm, 4u, 1.5 mL per min, 30° C., gradient 5-100% acetonitrile (+0.085% TFA) in water (+0.1% TFA) over 7 min—held for 30 s, 200-300 nm): Retention time 4.20 min, 99.00%.

LCMS (Phenomenex Synergi, RP-Hydro, 150×4.6 mm, 4u, 1.5 mL per min, 30° C., gradient 5-100% acetonitrile (+0.085% TFA) in water (+0.1% TFA) over 7 min—held for 30 s, 200-300 nm): Retention time 5.91 min, 100%, ES+: 410.484 [MH]+.

EXAMPLE 19

Preparation of (2R,3R,4R,5R)-5-(6-amino-2-{[(1S)-1-methylpropyl]amino}-9H-purin-9-yl)-2-(hydroxymethyl)-4-methoxytetrahydrofuran-3-ol 18

Scheme 18

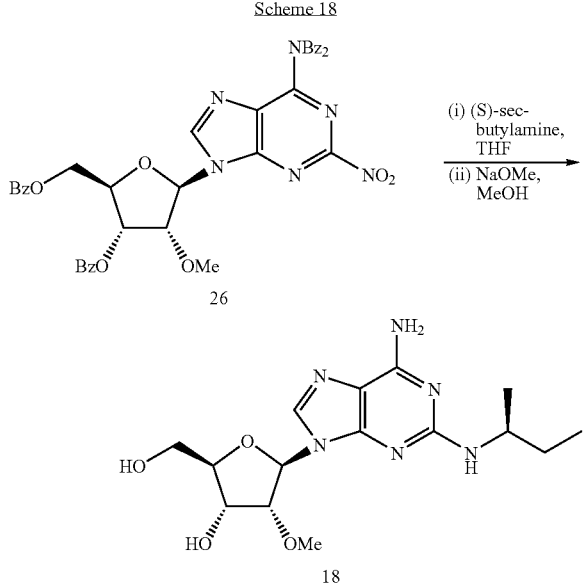

To a solution of 26 (445 mg, 0.64 mmol) in THF (8 mL) was added (S)-sec-butylamine (120 μL, 1.18 mmol) and further THF (8 mL). Stirring was continued for 1 wk and the solvents were then removed in vacuo. The residue was dissolved in methanol (8 mL), NaOMe (cat) was added and the resulting mixture was stirred for 2 d. Further NaOMe (cat) was added and the resulting mixture was stirred for 1 d before being concentrated in vacuo. The residue was dissolved in acetonitrile/water (1:1, 3 mL) and TFA/water (1:1, 0.5 mL) was added. This solution was purified by reverse phase column chromatography (LiChroprep RP-18, 40-63 μm, 230×26 (50 g), 30 mL per min, gradient 5-100% methanol in water over 30 min) and reverse phase prep HPLC (Phenomenex Synergi, RP-Hydro 150×10 mm, 10μ, 20 mL per min, gradient 5-100% acetonitrile in water over 10 min, product eluted in 37% acetonitrile) in 2 batches to yield (2R,3R,4R,5R)-5-(6-amino-2-{[(1S)-1-methylpropyl]amino}-9H-purin-9-yl)-2-(hydroxymethyl)-4-methoxytetrahydrofuran-3-ol 18 as a white solid (6.5 mg, 3%).

HPLC (Phenomenex Synergi, RP-Hydro, 150×4.6 mm, 4u, 1.5 mL per min, 30° C., gradient 5-100% acetonitrile (+0.085% TFA) in water (+0.1% TFA) over 7 min—held for 30 s, 200-300 nm): Retention time 3.54 min, 99.23%.

LCMS (Phenomenex Synergi, RP-Hydro, 150×4.6 mm, 4u, 1.5 mL per min, 30° C., gradient 5-100% acetonitrile (+0.085% TFA) in water (+0.1% TFA) over 7 min—held for 30 s, 200-300 nm): Retention time 4.52 min, 98.40%, ES⁺: 353.426 [MH]⁺.

EXAMPLE 20

Preparation of (2R,3R,4S,5R)-2-[6-amino-2-(hexylamino)-9H-purin-9-yl]-5-methyltetrahydrofuran-3,4-diol 19

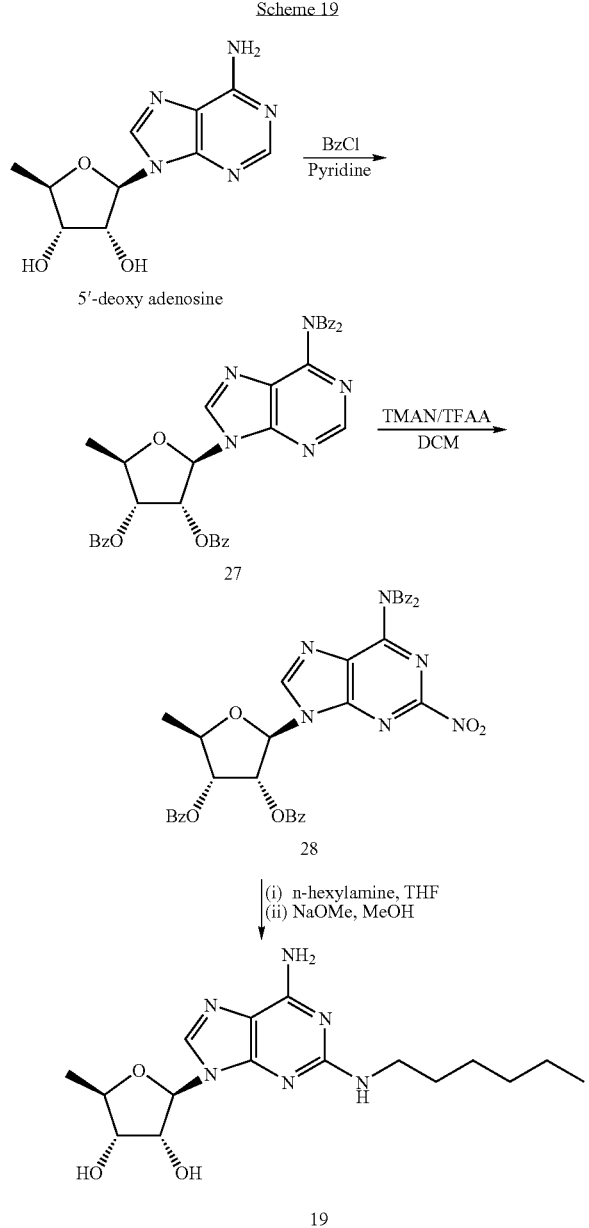

To a solution of 5′-deoxy adenosine (600 mg, 2.39 mmol) in pyridine (15 mL) was added benzoyl chloride (1.8 mL, 15.5 mmol) and the reaction heated at 80° C. for 5.5 h. After cooling to rt, the residue was concentrated in vacuo and dissolved in EtOAc (50 mL). The organic fraction was washed with 0.2M aq. HCl (25 mL), aq. NaHCO$_3$ (25 mL×2) and brine (25 mL) and dried over MgSO$_4$. Purification by flash column chromatography (normal phase, ICN silica, 18-32%, gradient 10-67% EtOAc in heptane, product eluted in 67% EtOAc) afforded 27 as a white foam (1.4 g, 88%).

To a suspension of TMAN (0.64 g, 5.35 mmol) in DCM (25 mL) was added TFAA (0.76 mL, 5.35 mmol) and the resulting solution was stirred for 3 h, cooled to 0° C. and a solution of 27 (2.38 g, 3.56 mmol) in DCM (25 mL) was added. The resulting solution was allowed to warm to rt over 16 h and the solvents were removed in vacuo. The residue was partitioned between EtOAc (100 mL) and water (75 mL) and the organic fraction was washed with brine (50 mL) and dried over MgSO$_4$. Crystallisation from DCM/ethanol afforded 28 as a pale yellow solid in 2 batches (1.10 g and 0.95 g, 81% overall).

To a solution of 28 (300 mg, 0.42 mmol) in THF (15 mL) was added n-hexylamine (111 μL, 0.84 mmol) and stirring was continued for 2 d. The solvents were then removed in vacuo and the residue was dissolved in methanol (10 mL). NaOMe (50 mg, 0.93 mmol) was added and the resulting mixture was stirred for 1 d. The solvents were removed in vacuo and the residue was purified by reverse phase column chromatography (LiChroprep RP-18, 40-63 μm, 230×26 mm (50 g), 30 mL per min, gradient 5-100% methanol in water over 30 min, product eluted in 70% methanol) and reverse phase prep HPLC (Phenomenex Synergi, RP-Hydro 150×10 mm, 10μ, 20 mL per min, gradient 5-100% acetonitrile in water over 14 min, product eluted in 37% acetonitrile) to yield (2R,3R,4S,5R)-2-[6-amino-2-(hexylamino)-9H-purin-9-yl]-5-methyltetrahydrofuran-3,4-diol 19 as a pale yellow solid (13.8 mg, 9%).

HPLC (Phenomenex Synergi, RP-Hydro, 150×4.6 mm, 4u, 1.5 mL per min, 30° C., gradient 5-100% acetonitrile (+0.085% TFA) in water (+0.1% TFA) over 7 min—held for 30 s, 200-300 nm): Retention time 4.46 min, 99.24%.

LCMS (Phenomenex Synergi, RP-Hydro, 150×4.6 mm, 4u, 1.5 mL per min, 30° C., gradient 5-100% acetonitrile (+0.085% TFA) in water (+0.1% TFA) over 7 min—held for 30 s, 200-300 nm): Retention time 6.12 min, 100%, ES⁺: 351.535 [MH]⁺.

EXAMPLE 21

Preparation of (2R,3R,4S,5R)-2-[6-amino-2-(cyclopentylamino)-9H-purin-9-yl]-5-methyltetrahydrofuran-3,4-diol 20

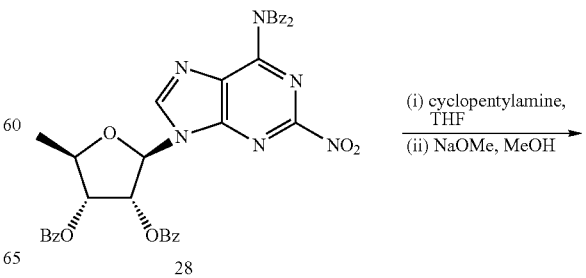

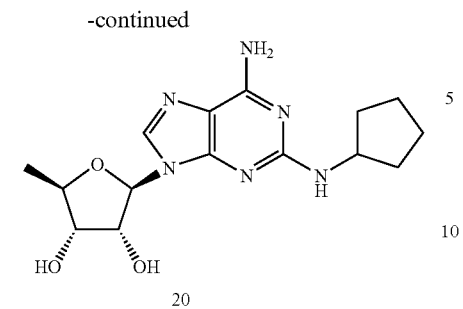

20

To a solution of 28 (600 mg, 0.84 mmol) in THF (15 mL) was added cyclopentylamine (166 µL, 1.69 mmol) and stirring was continued for 2 d. The solvents were then removed in vacuo and the residue was dissolved in methanol (10 mL). NaOMe (cat) was added and the resulting mixture was stirred for 16 h. The solvents were removed in vacuo and the residue was purified by reverse phase column chromatography (Li-Chroprep RP-18, 40-63 µm, 230×26 mm (50 g), 30 mL per min, gradient 0-100% methanol in water over 45 min, product eluted in 62% methanol) and twice by reverse phase prep HPLC (Phenomenex Synergi, RP-Hydro 150×10 mm, 10µ, 20 mL per min, gradient 5-100% acetonitrile in water over 25 min, product eluted in 35% acetonitrile) to yield (2R,3R,4S,5R)-2-[6-amino-2-(cyclopentylamino)-9H-purin-9-yl]-5-methyltetrahydrofuran-3,4-diol 20 as a pale yellow solid (8 mg, 3%).

HPLC (Phenomenex Synergi, RP-Hydro, 150×4.6 mm, 4u, 1.5 mL per min, 30° C., gradient 5-100% acetonitrile (+0.085% TFA) in water (+0.1% TFA) over 7 min—held for 30 s, 200-300 nm): Retention time 3.70 min, 99.51%.

LCMS (Phenomenex Synergi, RP-Hydro, 150×4.6 mm, 4u, 1.5 mL per min, 30° C., gradient 5-100% acetonitrile (+0.085% TFA) in water (+0.1% TFA) over 7 min—held for 30 s, 200-300 nm): Retention time 5.48 min, 100%/, ES$^+$: 335.404 [MH]$^+$.

EXAMPLE 22

Preparation of (2R,3R,5S)-2-[6-amino-2-(cyclopentylamino)-9H-purin-9-yl]-5-(hydroxymethyl)tetrahydrofuran-3-ol 21

Scheme 21

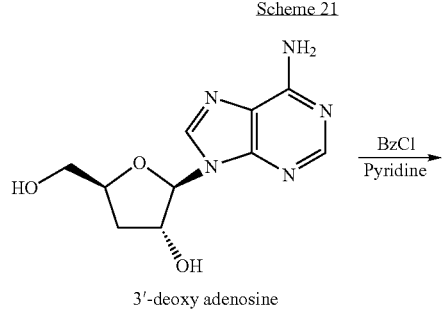

3'-deoxy adenosine

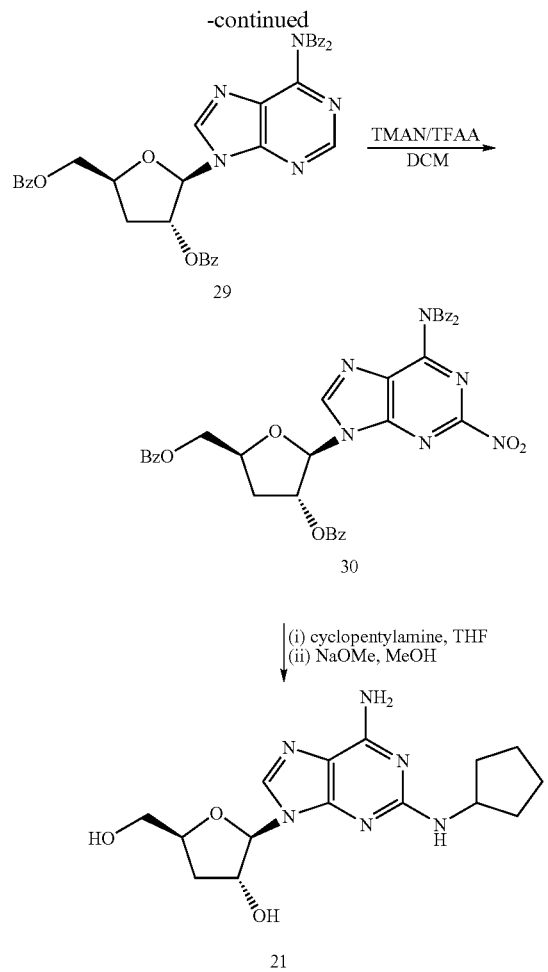

To a solution of 3'-deoxy adenosine (506 mg, 2.01 mmol) in pyridine (15 mL) was added benzoyl chloride (1.5 mL, 12.93 mmol) and the resulting solution was refluxed at 80° C. for 4 h. This procedure was then repeated on the same scale and both batches were combined and the solvents were removed in vacuo. The residue was dissolved in EtOAc (100 mL) and washed with 0.2M aq. HCl (50 mL), aq. NaHCO$_3$ (50 mL) and brine (50 mL), and the organic phase dried over MgSO$_4$. Crystallisation from DCM/ethanol afforded 29 as a white crystalline solid (2.38 g, 88%, >97% purity by HPLC).

To a suspension of 29 (668 mg, 1.00 mmol) and TMAN (156 mg, 1.3 mmol) in DCM (5 mL) was added dropwise a solution of TFAA (170 µL, 1.20 mmol) in DCM (1 mL) and the resulting solution stirred for 2 h. A solution of TFAA (28.3 µL, 0.20 mmol) in DCM (0.5 mL) was then added dropwise and stirring continued for a further 1 h. A further solution of TFAA (28.3 µL, 0.20 mmol) in DCM (0.5 mL) was added dropwise and following stirring for a further 1 h, the reaction mixture was quenched with aq. NaHCO$_3$ (4 mL). The organic phase was washed with water (30 mL×2), the combined aq. layers were washed with DCM (20 mL) and the combined organic extracts were dried over Na$_2$SO$_4$ to afford 30 as a yellow solid (563 mg, 79%, ~90% purity) which was used without further purification.

To a solution of 30 (320 mg, 0.40 mmol) in THF (7 mL) was added cyclopentylamine (80 µL, 0.81 mmol) and stirring continued for 16 h before further cyclopentylamine (80 µL, 0.81 mmol) was added. After 16 h, the solvents were removed in vacuo and the residue was dissolved in methanol (7 mL). NaOMe (cat) was added and the resulting mixture was stirred for 3 d. The solvents were then removed in vacuo and the residue was dissolved in acetonitrile/water (1:1, 3 mL) and TFA/water (1:1, 0.5 mL) was added. This solution was purified by reverse phase column chromatography (LiChroprep RP-18, 40-63 µm, 230×26 mm (50 g), 30 mL per min, gradient 5-100% methanol in water over 30 min, product eluted in 60% methanol), twice by reverse phase prep HPLC (Phenomenex Synergi, RP-Hydro 150×10 mm, 10µ, 20 mL per min, gradient 5-100% acetonitrile in water over 10 min, product eluted in 30% acetonitrile) and again by reverse phase prep HPLC (Phenomenex Synergi, RP-Hydro 150×10 mm, 10%, 20 mL per min, gradient 5-100% acetonitrile in water over 10 min, product eluted in 30% acetonitrile) to yield (2R,3R,5S)-2-[6-amino-2-(cyclopentylamino)-9H-purin-9-yl]-5-(hydroxymethyl)tetrahydrofuran-3-ol 21 as a white solid (1.6 mg, 1%).

HPLC (Phenomenex Synergi, RP-Hydro, 150×4.6 mm, 4u, 1.5 mL per min, 30° C., gradient 5-100% acetonitrile (+0.085% TFA) in water (+0.1% TFA) over 7 min—held for 30 s, 200-300 nm): Retention time 3.56 min, 99.39%.

LCMS (Phenomenex Synergi, RP-Hydro, 150×4.6 mm, 4u, 1.5 mL per min, 30° C., gradient 5-100% acetonitrile (+0.085% TFA) in water (+0.1% TFA) over 7 min—held for 30 s, 200-300 nm): Retention time 5.37 min, 97.87%, ES$^+$: 335.404 [MH]$^+$.

EXAMPLE 23

Plasma concentrations of spongosine were determined after single oral dosing in 5 or 6 human volunteers. Tachycardia was determined using 12 lead ECGs. The minimum effective analgesic plasma concentration in the rat was 0.025 µM suggesting a minimum effective dose in the human would be approximately 0.8 mg which results in plasma concentrations greater than 0.025 µM for approximately 1.5 h.

| Dose | Plasma Cmax (µM) | Tachycardia side effect |
| --- | --- | --- |
| 0.2 mg | 0.01 ± 0.005 | No |
| 0.8 mg | 0.04 ± 0.02 | No |
| 3.5 mg | 0.13 ± 0.04 | No |
| 10.5 mg | 0.3 ± 0.04 | No |
| 21 mg | 0.5 ± 0.1 | No |
| 28 mg | 0.6 ± 0.1 | Yes |

The invention claimed is:

1. A compound of the following general formula:

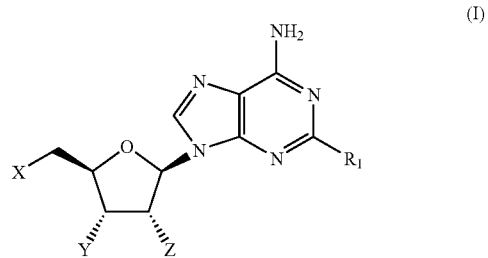

wherein:
when X=Y=Z=OH, R1 is OCH2CF2CF3, phenoxy (substituted with 3-(4-trifluoromethylphenyl), 3,4-dichloro, (3-trifluoromethyl,4-fluoro), (3-trifluoromethyl,4-chloro), (3-chloro, 4-cyano), or 3,5-bis(trifluoromethyl)), 1-piperazinyl(4-(3,4-dichlorophenyl)), phenyl (substituted with 3,4-dichloro, 3,5-difluoro, 3,5-bis(trifluoromethyl) or 3,4,5-trifluoro) or 2-benzofuranyl; or
when X=H and Y=Z=OH, R1 is n-hexylamino or cyclopentylamino; or
when X=Z=OH and Y=H, R1 is cyclopentylamino;
or a pharmaceutically acceptable salt thereof.

2. A compound according to claim 1, wherein each of X, Y and Z is OH.

3. A pharmaceutical composition comprising a compound according to claim 1, and a physiologically acceptable carrier, excipient, or diluent.

4. The pharmaceutical composition according to claim 3, further comprising an NSAID or a DMARD.

5. The pharmaceutical composition according to claim 3, further comprising an anti-pathogenic agent.

* * * * *